United States Patent
Morimoto

(10) Patent No.: US 7,035,856 B1
(45) Date of Patent: Apr. 25, 2006

(54) SYSTEM AND METHOD FOR TRACKING AND ROUTING SHIPPED ITEMS

(76) Inventor: Nobuyoshi Morimoto, 29-10-106, Sakuragaoka-cho, Shibuya-ku, Tokyo (JP) 150-0031

(*) Notice: Subject to any disclaimer, the term of this patent is extended or adjusted under 35 U.S.C. 154(b) by 930 days.

(21) Appl. No.: 09/675,258

(22) Filed: Sep. 28, 2000

(51) Int. Cl.
G06F 7/00 (2006.01)
G06F 17/30 (2006.01)
G06F 17/60 (2006.01)

(52) U.S. Cl. .......................................... 707/10; 705/8

(58) Field of Classification Search .................. 707/1, 707/10, 102; 705/1, 26, 28, 7, 8, 6, 9; 342/357
See application file for complete search history.

(56) References Cited

U.S. PATENT DOCUMENTS

| | | | |
|---|---|---|---|
| 4,799,156 A * | 1/1989 | Shavit et al. ................. | 705/26 |
| 5,015,145 A | 5/1991 | Angell et al. | |
| 5,038,283 A * | 8/1991 | Caveney ...................... | 705/28 |
| 5,063,506 A | 11/1991 | Brockwell et al. | |
| 5,117,096 A | 5/1992 | Bauer et al. | |
| 5,123,541 A | 6/1992 | Giannini et al. | |
| 5,261,282 A | 11/1993 | Grabowski et al. | |
| 5,413,236 A | 5/1995 | Kenevan | |
| 5,466,030 A | 11/1995 | Harris et al. | |
| 5,522,471 A | 6/1996 | Hilgendorf | |
| 5,565,858 A | 10/1996 | Guthrie | |
| 5,627,517 A * | 5/1997 | Theimer et al. ......... | 340/572.1 |
| 5,666,493 A | 9/1997 | Wojcik et al. | |
| 5,686,888 A * | 11/1997 | Welles et al. .......... | 340/539.13 |
| 5,712,788 A * | 1/1998 | Liaw et al. .................. | 701/209 |
| 5,715,398 A * | 2/1998 | Lubenow et al. .............. | 705/7 |
| 5,765,707 A | 6/1998 | Kenevan | |
| 5,804,810 A | 9/1998 | Woolley et al. | |
| 5,949,876 A | 9/1999 | Ginter et al. | |

(Continued)

FOREIGN PATENT DOCUMENTS

DE 44 46 203 6/1996

(Continued)

OTHER PUBLICATIONS

WO 02/19046 A1.*

(Continued)

Primary Examiner—Safet Metjahic
Assistant Examiner—Merilyn Nguyen
(74) Attorney, Agent, or Firm—Robert C. Kowert; Meyertons, Hood, Kivlin, Kowert & Goetzel, P.C.

(57) ABSTRACT

A method and system for shipping items. A server is configured to send out requests for quotes to a number of regional shipping companies using a network. The server receives responses from the network and selects a route based on the responses. The route may include shipping the item to one or more intermediate destinations before the item arrives at the final destination. The server may create a data file reflecting the selected route. The items are packed in one or more containers, wherein each container has a memory device. At least part of the data file is then stored into the memory device. The memory device may be accessed as needed during shipping to determine where the item is going and when the item needs to arrive. Additional information may also be stored in the memory device, and the device may be updated at intermediate destinations. Each container may take a different routing, and the server may actively search for better routings as the item proceeds along the selected route. The containers may be configured to be placed within carriers that hold multiple containers, and the carriers may also be configured with memory devices.

52 Claims, 15 Drawing Sheets

U.S. PATENT DOCUMENTS

| | | | | |
|---|---|---|---|---|
| 5,959,568 | A | * | 9/1999 | Woolley ..................... 342/42 |
| 6,094,642 | A | * | 7/2000 | Stephenson et al. .......... 705/28 |
| 6,099,047 | A | | 8/2000 | Reiff et al. |
| 6,115,695 | A | | 9/2000 | Kern |
| 6,128,549 | A | | 10/2000 | Swartz et al. |
| 6,151,582 | A | | 11/2000 | Huang et al. |
| 6,199,046 | B1 | | 3/2001 | Heinzle et al. |
| 6,236,971 | B1 | | 5/2001 | Stefik et al. |
| 6,321,992 | B1 | * | 11/2001 | Knowles et al. ....... 235/462.01 |
| 6,332,098 | B1 | * | 12/2001 | Ross et al. .................. 700/226 |
| 6,356,802 | B1 | | 3/2002 | Takehara et al. |
| 6,398,109 | B1 | | 6/2002 | Ohki |
| 6,429,810 | B1 | * | 8/2002 | De Roche ............. 342/357.07 |
| 6,460,020 | B1 | * | 10/2002 | Pool et al. .................... 705/26 |
| 6,873,963 | B1 | * | 3/2005 | Westbury et al. .............. 705/8 |
| 2001/0043273 | A1 | | 11/2001 | Herrod et al. |
| 2003/0183697 | A1 | | 10/2003 | Porter |

FOREIGN PATENT DOCUMENTS

| | | |
|---|---|---|
| DE | 198 13 842 | 9/1999 |
| EP | 726447 A1 * | 8/1996 |
| EP | 854353 A2 * | 7/1998 |
| JP | 5-242106 A | 9/1993 |
| JP | 2001-171811 | 6/2001 |
| JP | 2001-253517 | 9/2001 |
| WO | 96/13015 | 5/1996 |
| WO | 99/23623 | 5/1999 |

OTHER PUBLICATIONS

"MSR Visual Exporter: Premium Global Export Software," 6 pgs., © 2001 MSR International, Inc.

Kumar et al., "Building the 'last mile'—how to solve logistics conflicts in e-business," © European Business Forum Limited 2000, pp. 66-70.

"Yusen Air & Sea Services (USA), Inc.," © 2001 Yusen Air & Sea Service Co., Ltd., pp. 1-6.

"FedEx Tracking," © 1995-2001 FedEx, pp. 1-2.

"UPS Handheld Solutions," © 1994-2000 United Parcel Service of America, Inc., pp. 1-2.

"UPS Shipping and Tracking Solutions," © 1994-2000 United Parcel Service of America, Inc., pp. 1-3.

"UPS OnLine WorldShip," © 1994-2000 United Parcel Service of America, Inc., pp. 1-4.

"UPS OnLine Host Access," © 1994-2000 United Parcel Service of America, Inc., pp. 1-2.

"UPS OnLine Compatible Solutions," © 1994-2000 United Parcel Service of America, Inc., pp. 1-4.

"Intrepa Products & Services," © 2000 Intrepa LLC, pp. 1-3.

"Shipment Packaging Software from Cargoware," © 1999 Cargoware, pp. 1-2.

Stenmark, "Information agents for the web," Feb. 1998, 2 pgs.

International Search Report for PCT/IB 01/02344, mailed May 15, 2002.

* cited by examiner

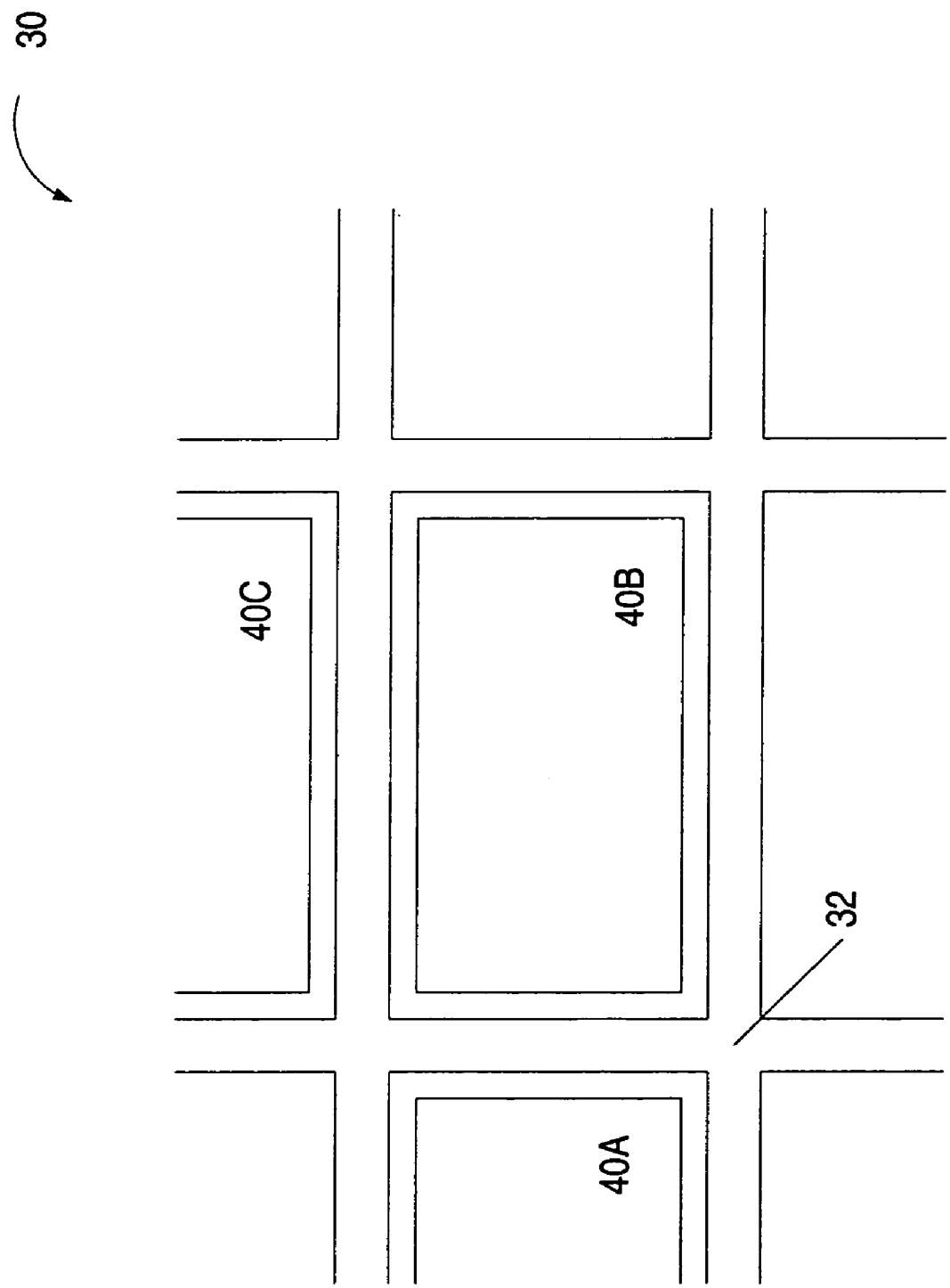

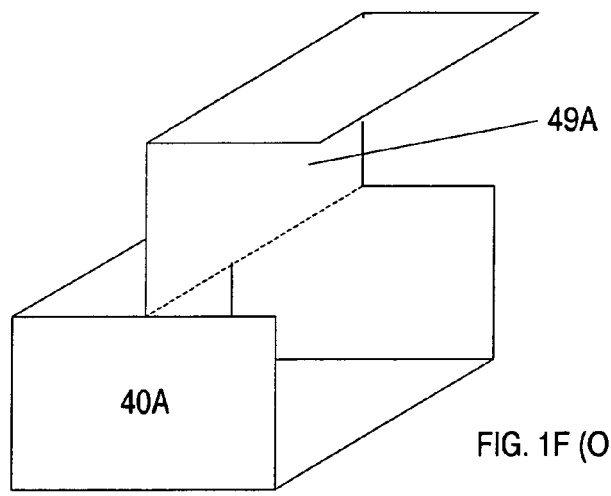
FIG. 1F (OPEN SIDE)
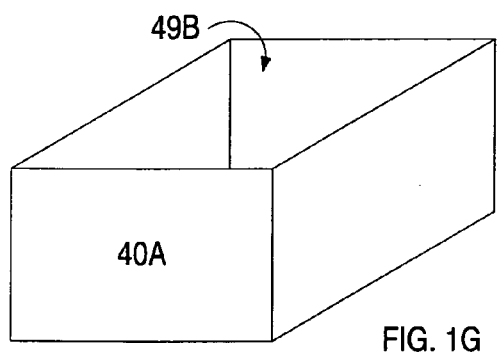
FIG. 1G (OPEN TOP)
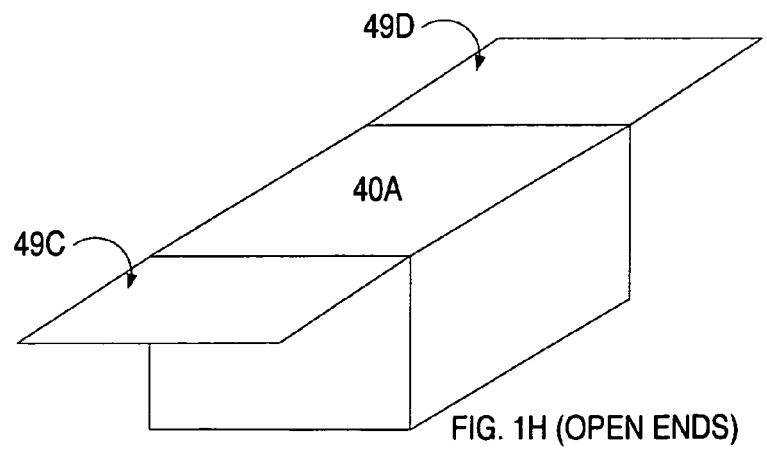
FIG. 1H (OPEN ENDS)

| | |
|---|---|
| Package/Item Tracking No. | |
| Description of Goods | |
| Weight | |
| Special Shipping Information (e.g., temperature restrictions) | |
| Insurance amount, terms (e.g., deductible) | |
| Ship Date | Arrival Deadline |
| Origination | Destination |
| Payment Terms | |
| Sender's Name | Sender's e-mail address |
| Sender's telephone | Sender's street address |
| Sender's Account Number | |
| Recipient's Name | Recipient's e-mail address |
| Recipient's telephone | Recipient's street address |
| Recipient's Account Number | |
| 1st Intermediate Destination | |
| 1st Intermediate Destination Arrival Date | |
| 1st Intermediate Destination Ship Date | |
| 1st Intermediate Destination Shipper Info | |
| 2nd Intermediate Destination | |
| 2nd Intermediate Destination Arrival Date | |
| 2nd Intermediate Destination Ship Date | |
| 2nd Intermediate Destination Shipper Info | |
| 3rd Intermediate Destination | |
| 3rd Intermediate Destination Arrival Date | |
| 3rd Intermediate Destination Ship Date | |
| 3rd Intermediate Destination Shipper Info | |

FIG. 4

SYSTEM AND METHOD FOR TRACKING AND ROUTING SHIPPED ITEMS

BACKGROUND OF THE INVENTION

1. Field of the Invention

The present invention generally relates to the shipping of goods from one place to another. More particularly, the present invention relates to an automated system and method for tracking and routing the shipped goods.

2. Description of the Related Art

Internet commerce has become an increasingly popular form of commerce in the United States and throughout the world. In general, Internet-based commerce, often referred to as e-commerce, provides advantages to both suppliers and consumers. E-commerce provides vendors and service providers the ability to greatly increase their sales channel and distribution network with minimal cost. An Internet commerce site provides a convenient, effective and secure mechanism for potential buyers to browse, select and purchase goods or services in an easy and simple fashion.

However, Internet retailers face many obstacles to turning a profit. Chief among these obstacles are high shipping costs. For example, assuming an online retailer of compact disks (CDs) based in California sells a CD to a customer in New York for $12. The customer may be unwilling to pay $3 (i.e., 25% of the sales price) for shipping. Internet retailers of consumer goods such as CDs, videos, and consumables face a more difficult challenge than retailers of more expensive items such as jewelry. Consumers are less likely to object to paying a $3 shipping charge for a $100 necklace than for a $12 CD.

Taxes combine with shipping costs to influence online consumer purchasing decisions. Currently, many Internet retailers do not charge their customers sales tax, which tends to offset the high shipping costs to some extent. However, sales tax is typically less than 10% of the sales price, thus to stay competitive with their prices, Internet retailers must strive to price their items at least 15% lower than traditional brick-and-mortar retail stores. Furthermore, the future of current moratoriums on Internet sales taxes remains uncertain. It is likely that traditional brick-and-mortar retailers will exert considerable pressure on federal and state governments to "even the playing field" by forcing Internet retailers to pay some sort of Internet sales tax. For this reason, the importance of reducing shipping costs may be even more critical in the near future. Thus, a system and method for more efficiently handling and routing packages is needed.

SUMMARY OF THE INVENTION

The problems outlined above may at least in part be solved by a system and method for efficiently shipping items. As used herein, the terms "ship" and "shipping" shall include all types of conveyance, including using express carriers (e.g., Federal Express, Airborne, DHL), national postal services (e.g., the United States Postal Service and United Parcel Service), local delivery services (e.g., bicycle, motorcycle, car) and freight carriers (e.g., air, rail, ship, and truck).

In one embodiment, the system may include a software program configured to determine one or more efficient shipping routes for a particular package that is to be shipped. The program may be configured to determine shipping routes that utilize more than one shipping company or that include one or more intermediate destinations (as opposed to a direct route). For example, instead of shipping an item directly from Tokyo to New York for $100 using only one shipping company, the software program may determine that a better price may be had if shipping company A is used to ship the item from Tokyo to San Francisco for $50 and then shipping company B is used to ship the item from San Francisco to New York for $40.

The method described above may be implemented using a system of specialized shipping containers. The shipping containers may be of one or more standard sizes that allow them to be shipped together with other containers in a carrier. The use of carriers and shipping containers that fit within the carriers may advantageously simplify the shipping of items with one or more intermediate destinations. Using the above example, shipping company A may have standing arrangements with a first airline to ship one carrier from Tokyo to San Francisco on a daily basis. Similarly, shipping company B may have standing arrangements with a second airline to ship one carrier from San Francisco to New York on a weekly basis. By negotiating these standard arrangements, shipping companies A and B may obtain rates that are lower than the rates typically paid for one-time shipments.

When an item is to be shipped from Tokyo to New York, the item may be packaged in a shipping container that fits within a carrier. For example, the carrier may be configured to hold 9 individual containers in a 3×3 array. Shipping company A may place the container within a first carrier going from Tokyo to San Francisco. Once the carrier arrives in San Francisco, the particular container going to New York may be removed and may be placed into a second carrier going from San Francisco to New York by shipping company B. Since multiple containers fit in each carrier, shipping companies A and B may aggregate containers from different sources and with different final destinations to increase the utilization of space within each carrier. The shipping companies may communicate with each other via a computer network to negotiate rates for available space within carriers. A central server may be connected to the network to oversee the process and act as a central database for availability information and shipping rates.

Thus, using carriers that hold multiple shipping containers may simplify the process of shipping of items through one or more intermediate destinations. If the item to be shipped is too large for a single container, it may be shipped in two or more containers. However, each container may take a different route to the final destination and may arrive at a different time.

To increase the efficiency of the process at the transfer points or intermediate destinations (e.g., San Francisco in the above example), the containers and/or carriers may be configured with attached or embedded memory devices for storing information about the item(s) being shipped. This may advantageously simplify the process of transferring the carriers since the memory device may store routing and final destination information for the container, as well as other information such as: contact information for each shipping company that will handle the container, contact information for the person or company that originally sent the item, contact information for the person or company that is to be the final recipient of the item, a description of the item (so that the container does not have to be opened to identify its contents), a unique identifier (e.g., a container or shipping tracking number), any special handling requirements, the weight of the container, customs information, and insurance information.

In one embodiment, the memory device may be configured with a wireless interface (e.g., infrared or radio wave) that allows the contents of the memory device to be read and updated without physically contacting the device. This may simplify the transfer of the container at intermediate destinations and may also allow the information stored in the memory device to be updated as the container progresses through its designated routing. For example, at each intermediate destination, the shipping company may have a workstation or hand-held tracking device configured to update the information in the memory device (e.g., to reflect the time that the container was received). Other information may also be updated (e.g., the condition of the container and/or item).

While a traditional computer may be configured to interface with the memory device, in other embodiments more specialized equipment may be utilized (e.g., a hand-held apparatus that interfaces with the memory device using a wireless communications link. A conveyor belt-based apparatus may also be used. Additional functionality may also be built into the apparatus, such as a scale for weighting the container/carrier or a digital camera for taking pictures of the carrier/container/item to prove the condition of the item at the time the transfer is made. The apparatus may also be configured with a computer network interface that allows the information gathered to be distributed to multiple parties (e.g., providing shipping updates to the originating party and the recipient).

BRIEF DESCRIPTION OF THE DRAWINGS

The foregoing, as well as other objects, features, and advantages of this invention may be more completely understood by reference to the following detailed description when read together with the accompanying drawings in which:

FIG. 1B illustrates a close-up view of one embodiment of the container and carrier system from FIG. 1A;

FIGS. 1F–H illustrate details of different embodiments of the container from FIG. 1A;

FIG. 4 illustrates one embodiment of a data file that may be stored in a memory device attached to a container or carrier for shipping packages;

Figure 1A:
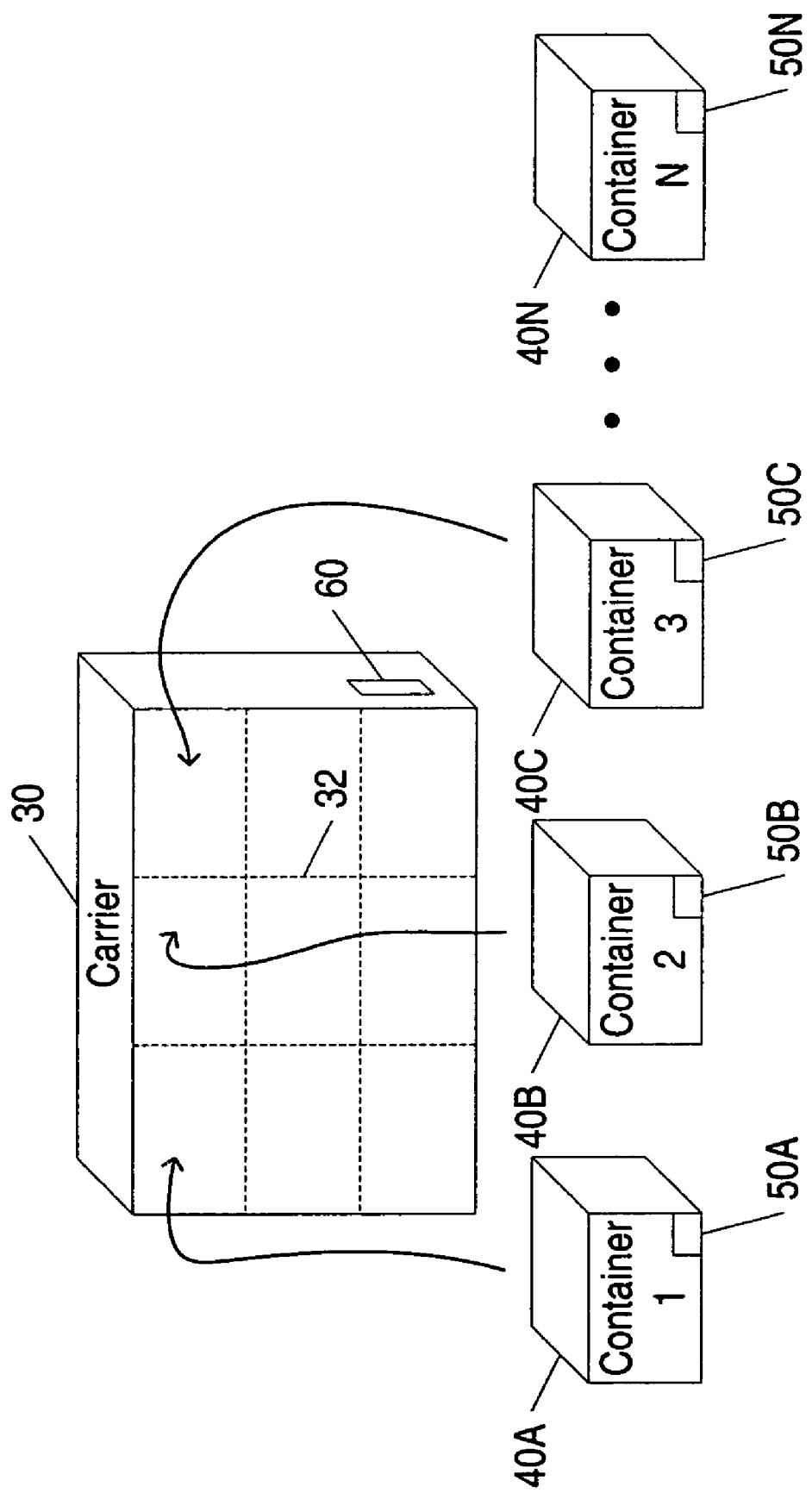
FIG. 1A illustrates one embodiment of a container and carrier system for efficiently transporting goods.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

Please note that the headings used herein are for organizational purposes only and are not meant to limit the description or claims. Further note that as used herein, the terms "package", "goods", and "item" are used interchangeably to refer to an item being shipped. Also note, the word "may" is used in this application in a permissive sense (i.e., having the potential to, being able to), not a mandatory sense (i.e., must).

DETAILED DESCRIPTION OF SEVERAL EMBODIMENTS

FIGS. 1A–K: Carrier and Containers

Turning now to FIG. 1A, one embodiment of a carrier 30 configured to allow efficient shipping of goods is shown. In this embodiment, carrier 30 is configured to store a number of individual containers 40A through 40N. Carrier 30 may be configured to allow each individual container to be inserted or removed on an individual basis. Carrier 30 may be configured with a memory 60 that is configured to store electronic data. Similarly, containers 40A through 40N may also be configured with memory devices 50A through 50N, respectively. Memory 60 may be configured to store various information corresponding to carrier 30 (and possibly containers 40A–N stored within carrier 30). Similarly, memory devices 50A through 50N may be configured to store electronic data corresponding to containers 40A through 40N, respectively. Carrier 30 may be constructed of a number of different materials, including plastic, wood, or aluminum. Carrier 30 may be configured with an internal frame 32 that allows containers 40A–N to be inserted securely within carrier 30. Frame 32 may advantageously prevent containers from shifting during shipping, e.g., if carrier 30 is not completely full of containers. Frame 32 may also include tracks or shelves with rollers that allow each container within the carrier to be inserted and removed more easily. While containers 40A–N are preferably the same size, in some configurations different container sizes may be made available for larger items to be shipped. For example, each standard container may be 0.5 m by 0.5 m by 1.5 m, with nine containers fitting in carrier 30 in a 3 by 3 configuration. However, a larger container measuring 1.0 m by 1.0 m by 1.5 m may be used for oversized items. This larger container may fit within carrier 30 with up to five of the standard containers. Other configurations and sizes are also possible and contemplated (e.g., a 3×3×2 arrangement of containers within carrier 30, or containers measuring 20 feet by 40 feet). The containers may be configured to meet industry standard requirements such as strength, resilience, durability, and a lack of hidden compartments (i.e., to address smuggling concerns).

In one embodiment, memory 60 may be configured to store a unique item identification number (e.g., a serial number) for carrier 30. Memory 60 may also be configured to store origination information and final destination information for carrier 30. For example, carrier 30 may be shipped from Tokyo to New York, and memory 60 may be configured to store that information. Various additional information may also be stored in memory 60 (e.g., container identification numbers for each container stored within carrier 30). If carrier 30 is shipped to one or more intermediate destinations (e.g., from Tokyo to New York via Chicago), then information regarding the intermediate destination may also be stored in memory 60. Other information about carrier 30 (and containers 40A–N within carrier 30) may also be stored in memory 60. For example, the contents of each container 40A–N may be stored in memory 60. Insurance and customs information may also be stored in memory 60.

Memory devices 50A–N may be configured similarly to memory device 60. For example, in one embodiment memory device 50A may be configured to store origination information, intermediate destination information, and final destination information for container 40A. Memory device 50B may store similar information for container 40B. The memory devices may be implemented using a number of different technologies (e.g., Flash memory, SRAM, DRAM, EEPROM, hard drive, removable optical or magnetic media). The memory devices may have a power supply (e.g., a battery, solar panel, or both) connected to it (e.g., in the case of DRAM), or it may rely on the power supply of the processing unit at the shipping location to provide the necessary power to perform reads and writes. The memory devices may also include interface logic (e.g., transceivers and memory controllers) and appropriate connectors (e.g., RS-232 or universal serial bus (USB)) to control the read and write process. In some embodiments, the memory devices may further include a wireless interface (e.g., infrared or radio wave) to allow the contents of the memory devices to read and written to without requiring a physical connection to the device.

In yet another embodiment, barcode stickers may be used as a memory device. In this embodiment, the barcode may be printed out on a sticker and subsequently affixed to the container and/or carrier. Additional data may be printed out on additional stickers and affixed to the container and/or carrier near the previous sticker. The information may be read by a barcode scanner which is configured to read all of the barcodes affixed on the carrier or container. In the event that some of the data needs to be overwritten, additional barcode stickers may be printed out and affixed to the container or carrier over the preceding barcode stickers. Advantageously, this may provide an inexpensive read-write memory device.

Depending on the embodiment, however, the memory device need not be physically attached to the container or carrier. For example, the memory device may be implemented as a small electronic component (e.g., encased in plastic) designed to packed inside the container with the goods being shipped.

In embodiments that utilize active memory devices (e.g., electronic or magnetic memory as opposed to barcodes, which are a passive memory), additional features such as global positioning and environmental (e.g., temperature, humidity, vibration) sensing may also be implemented as part of the memory devices. For example, the memory device for a particular container may include a microprocessor (or microcontroller) and a temperature sensor. The microprocessor may be configured to periodically sample the temperature readings from the sensor. If the temperature exceeds a predetermined threshold (e.g., too low or too high), then the processor may store an indication of this (e.g., the exact temperature and the time that the event took place) in the memory device. Alternatively, the processor may be configured to store all periodic temperature readings in the memory device, thereby providing the recipient and the shipping company with a complete log of the temperatures experiences by the container throughout the shipping process. Taking the wireless connection one step further, the memory device may be configured with a long-range wireless communications device (e.g., with a cellular or PCS telephone link, satellite link, or other wireless network protocol) to allow the memory device to periodically upload the temperature information and the data file to central server 90. Other possibilities include an optional GPS (global positioning system) sensor that can store position information for the container. Currently, the cost of long-range wireless communications and GPS sensors may be prohibitive, but if prices continue to drop, these may become more economical options. The memory device may also store digital images of the items being shipped (e.g., as the items are being packed to prove that the items are in good condition before shipment).

Advantageously, the configuration of carrier 30 and containers 40A–N shown in the figure may allow for efficient shipping of goods. For example, regional shipping companies may make arrangements to have a carrier such as carrier 30 routinely shipped on certain flights from a particular origination to a particular destination (e.g., from San Francisco to Dallas, and from Dallas to New York). A regional shipping company based in San Francisco may make arrangements with one or more airlines so that the airlines will carry one carrier from San Francisco to Dallas per day. Similarly, a carrier based in New York may make a similar arrangement with one or more airlines to carry a carrier from Dallas to New York on a daily basis. As noted above, this type of shipping arrangement may advantageously result in lower shipping costs. If each regional shipping company uses a standard carrier (e.g., carrier 30) and standard containers (e.g., containers 40A through N), then a customer having one or more containers to be shipped from San Francisco to New York may be able to have the containers inserted into the first shipping company's carrier going from San Francisco to Dallas, and then have the containers transferred to the second carrier going from Dallas to New York. In some cases, this routing may be cheaper than a direct routing from San Francisco to New York.

In some embodiments, this method for shipping may be analogized to the packet switching performed in IP or telephone networks. In a traditional telephone system, a dedicated circuit was established between the caller and recipient for each call. This mirrors traditional shipping in which a customer makes an arrangement with a single shipping company for shipment of an item from an origination point to a final destination. However, in recent years the telephone company digitizes the voice at either end of a telephone call and breaks the information into packets. These packets are then routed individually from the origination to the destination. For a single call, one packet might be routed through Chicago, while the following packet may be routed through Dallas. Similarly, a customer having to ship twelve containers from San Francisco to New York may find a better price by breaking up the container shipments and routing the containers individually. Some containers may take a direct flight from San Francisco to New York, while others may be routed through Dallas or Chicago.

Advantageously, memory devices 50A–N and 60 may simplify the transfer of containers at intermediate destinations such as Dallas or Chicago in the example above. As noted above, in some embodiments each memory device may include a wireless transceiver configured to send and receive information to a processing unit. The processing unit may be used by the shipping company personnel at the intermediate destination to rapidly determine which containers need to be removed from which carriers, and which new carriers the containers should be inserted into.

Turning now to FIG. 1B, details of one embodiment of carrier 30 are shown. In this embodiment, containers 40A–C are configured to slide into carrier 32, and carrier 32 is configured to protect and secure each container 40A–C, even if the carrier is not completely full. As shown in the figure, carrier 30 may be formed as a rigid frame spaced so as to allow containers to be inserted and removed on an individual basis. Carrier 30 may be made of any suitable material, e.g., plastic, aluminum, carbon fiber, fiberglass, wood, or a combination thereof.

Figure 1C:
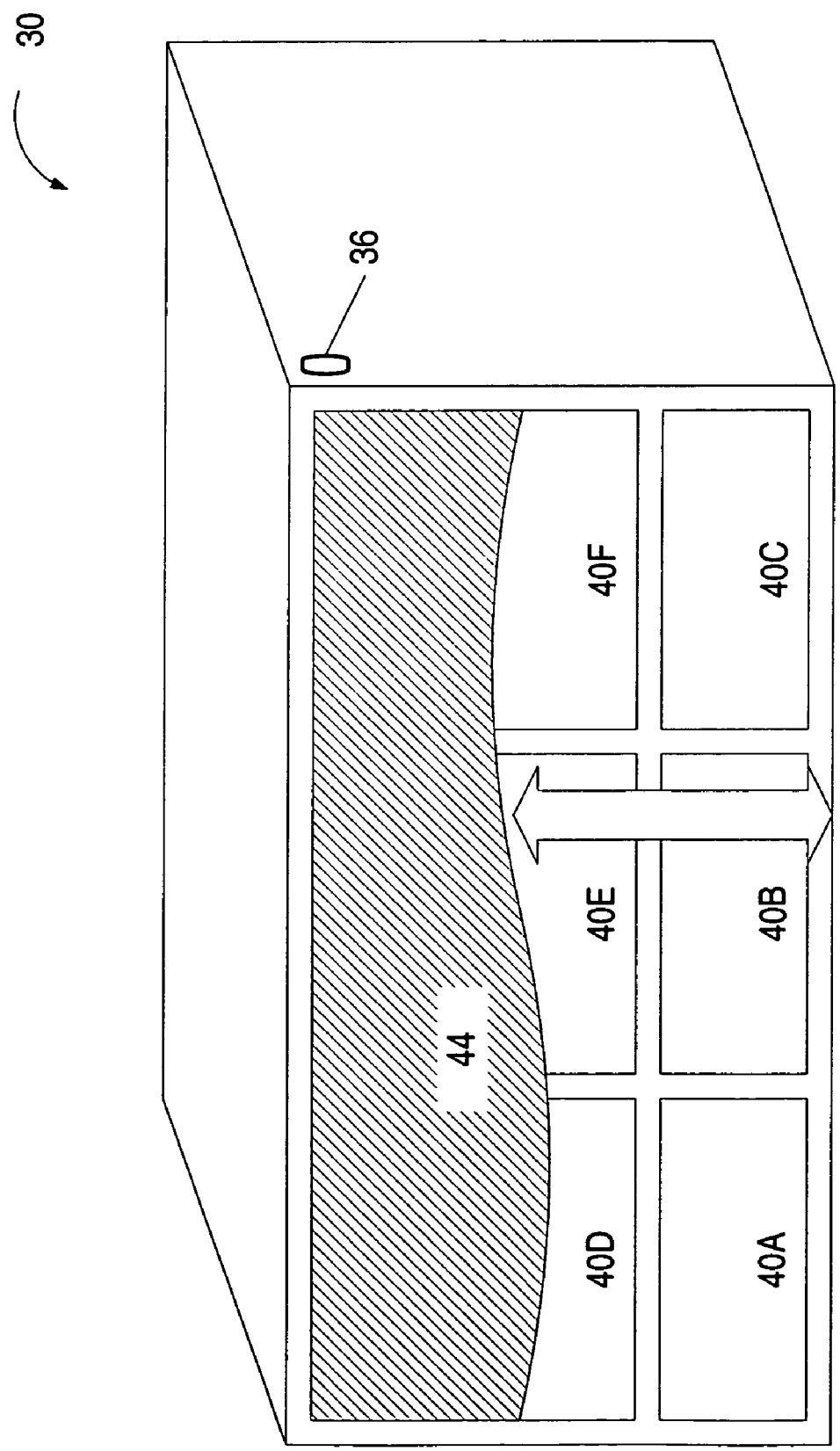
FIGS. 1C–E illustrate details of different embodiments of the container and carrier system from FIG. 1A.

Turning now to FIG. 1C, another embodiment of carrier 30 is shown. In this embodiment, carrier 30 includes a cover 44 and a rotating spool mechanism 36 that is configured to raise and lower cover 44. In some embodiments the cover may be raised and lowered manually (e.g., using a manual crank arm that is connected to spool mechanism 36). In other embodiments, spool mechanism may be an electric motor that is configured to automatically raise or lower cover 44. An internal battery may be included within carrier 30, or an external power source may be connected to spool mechanism 36. Cover 44 may be of any suitable material (e.g., cloth, nylon mesh, chain mesh) that prevents containers 40A–N from falling out of or being removed from carrier 30. Cover 44 may have a locking mechanism (e.g., a combination or a key lock) that prevents unauthorized handlers from removing or accessing containers in carrier 30.

Figure 1D:
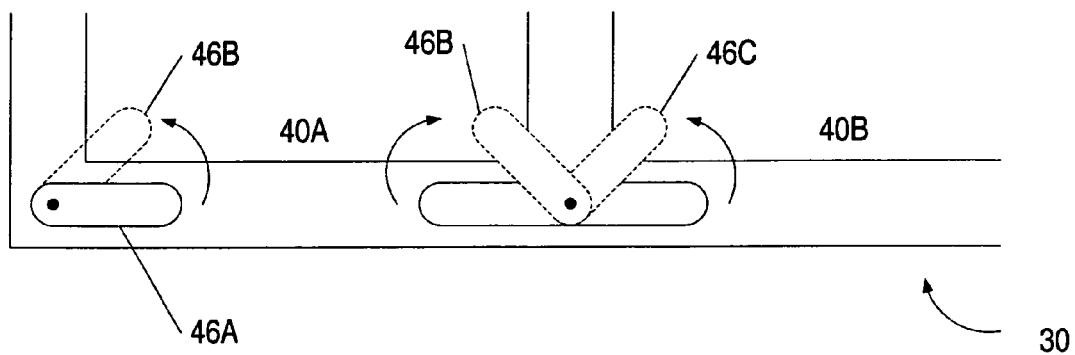

Turning now to FIG. 1D, details of a portion of one embodiment of carrier 30 are shown. In this embodiment, carrier 30 includes locking clips 46A–C which are coupled to carrier 30 in a moveable fashion. Locking clips 46A–C may be positioned either to allow the corresponding container (e.g., containers 40A and 40B) to be inserted or removed from carrier 30, or to prevent the containers from being removed. As with cover 44 in the previous embodiment, locking clips 46A–C may be configured to require a key or combination to prevent unauthorized removal or tampering.

Figure 1E:
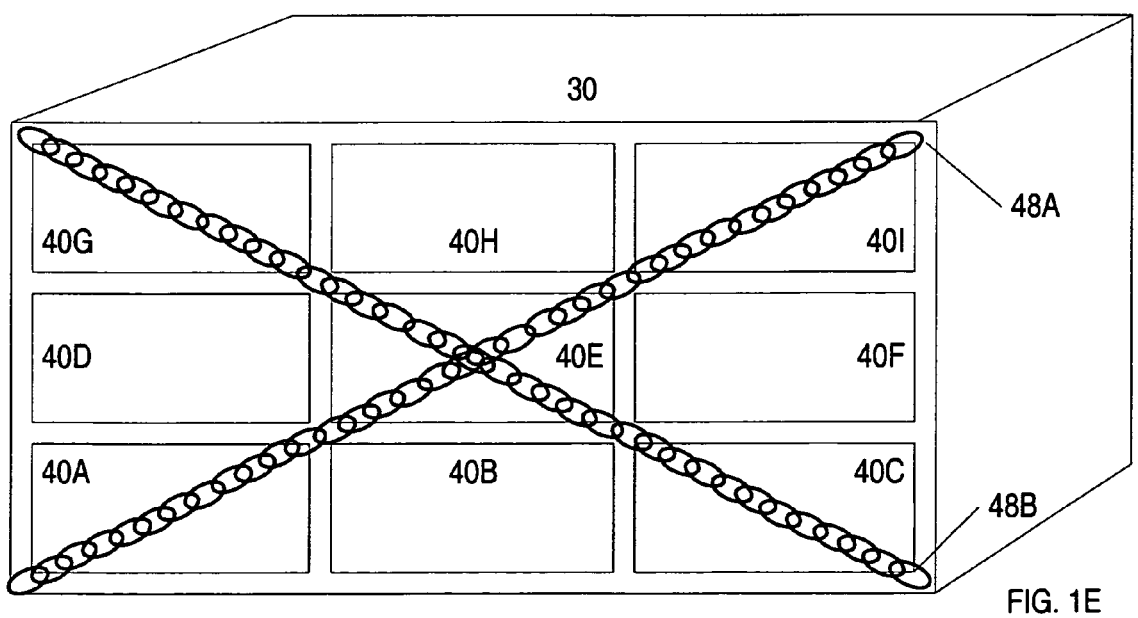

Turning now to FIG. 1E, another embodiment of carrier 30 is shown. In this embodiment, carrier 30 includes chains 48A–B that are configured to secure containers 40A–G into carrier 30. While a number of different configurations for carrier 30 have been described herein, other configurations are possible and contemplated. For example, combinations of locking clips 46A–C, chains 48A–B, and cover 44 may be used. Other fastening devices such as latches and lids that are configured to be bolted onto carrier 30 may also be used in addition to, or in lieu of, the configurations described above.

Turning now to FIGS. 1F–1H, a number of different configurations of container 40A are shown. Container 40A may be configured with a hinged top and side 49A, an open top 49B, or hinged sides 49C–D. The exact configuration of container 40A may vary based on the type of items being shipped or the configuration of carrier 30.

Figure 1J:
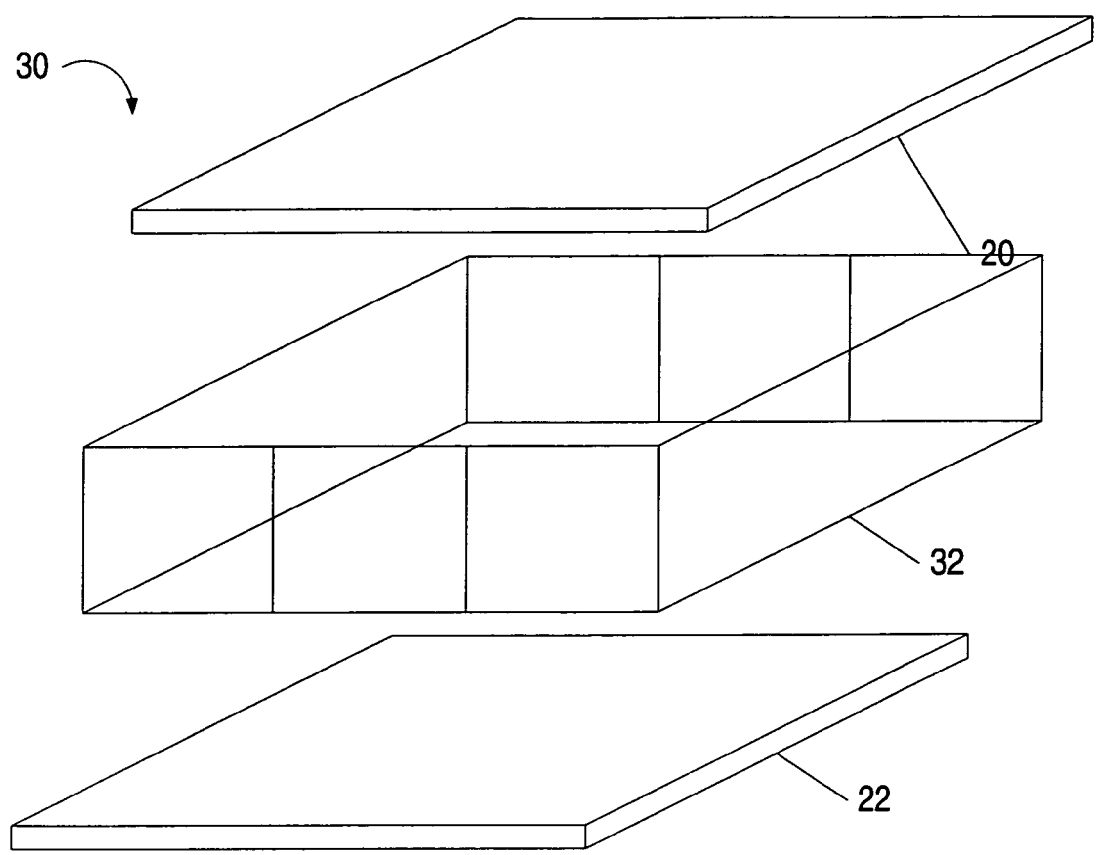
FIG. 1J illustrates one method for constructing the carrier system from FIG. 1A.

Turning now to FIG. 1J, one possible method for constructing carrier 30 is shown. In this embodiment, carrier 30 comprises a rigid frame 32 (e.g., constructed of metal such as aluminum) that provides strength to prevent compression damage, and top and bottom members 20–22, which provide additional strength to prevent bending or twisting of frame 32 or containers within frame 32. Top and bottom members 20–22 may be constructed of materials such as wood, plastic, fiberglass, or aluminum. Additional sides may also be attached to frame 32.

As noted earlier, containers 40A–G may be industry standard containers or customer containers also constructed of light yet strong material (e.g., plastic, wood, fiberglass, or aluminum). Containers 40A–G and/or carrier 30 may configured to be weather proof (e.g., water tight), to prevent damage to the items being shipped. Containers 40A–G are preferably constructed of material that is resilient enough so that each container may be shipped many times. Advantageously, this may reduce package costs and waste in the shipping process.

Figure 1K:
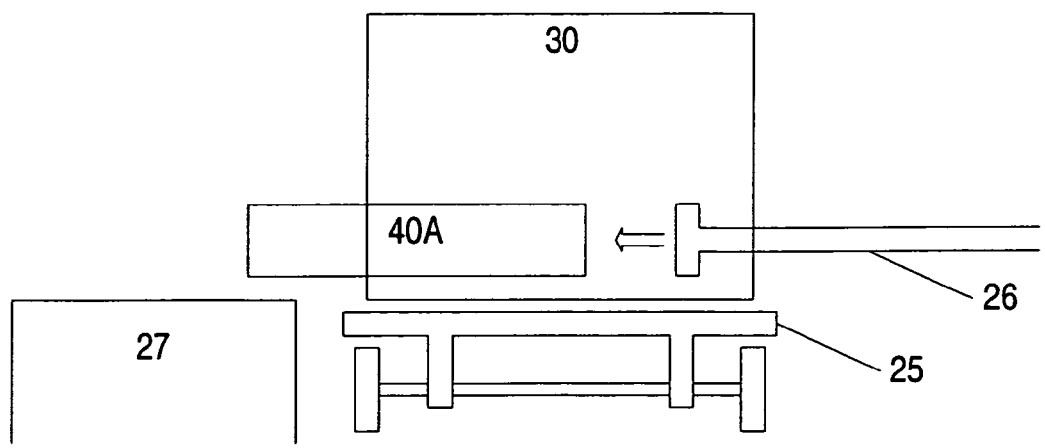
FIG. 1K illustrates one method for loading and unloading one embodiment of the container and carrier system from FIG. 1A.

Turning now to FIG. 1K, one embodiment of carrier 30 that allows automated packing and unpacking of containers is shown. In this embodiment, two opposing sides of container 30 are opened to allow an automated pusher arm 26 to push a selected container (i.e., container 40A in this example) onto a loading platform 27. As shown in the figure, the automated pusher arm 26 and loading dock 27 may be positioned so as to allow carrier 30 to be loaded and unloaded without being removed from the vehicle that is transporting the carrier (e.g., the rail car or flat bed trailer).

Figure 2:
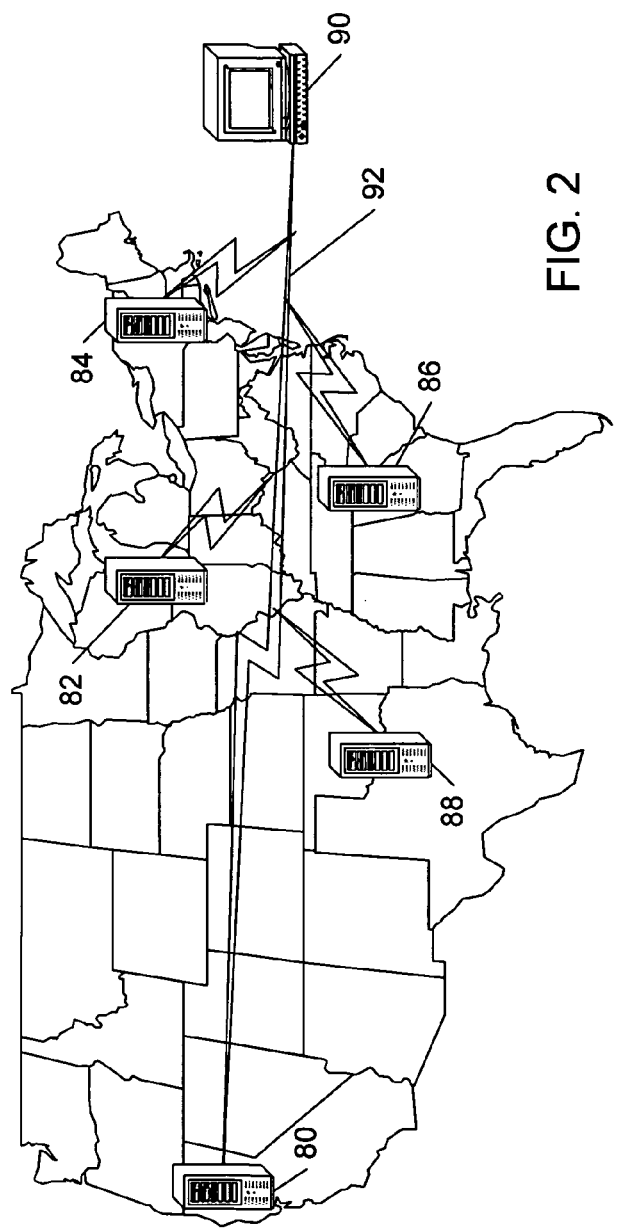
FIG. 2 illustrates one embodiment of a network of regional shipping locations, hubs, or transfer points.
Figure 3:
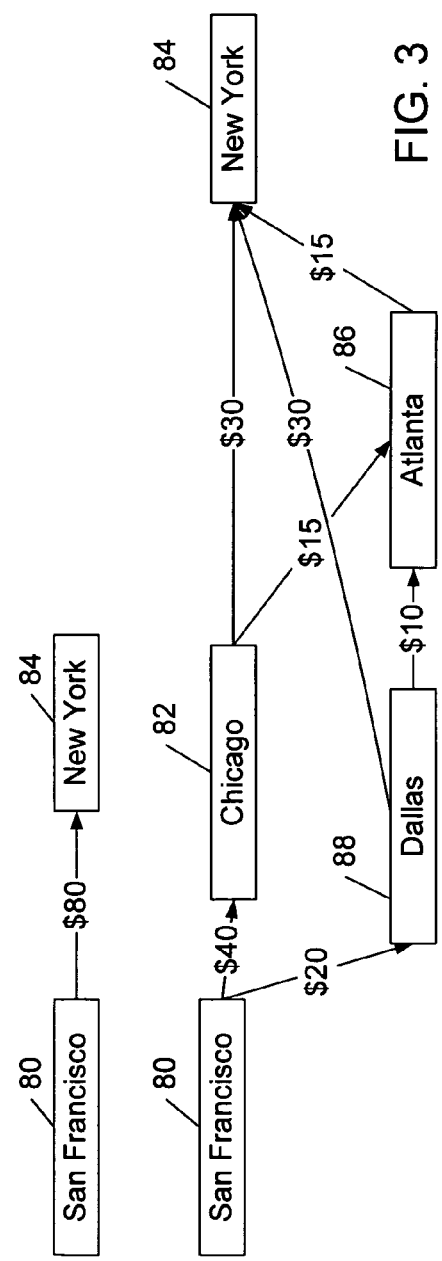
FIG. 3 illustrates how an indirect shipping route with one or more intermediate destinations may be less expensive than a direct shipping route.

FIGS. 2–3: Example of Efficient Shipping

Turning now to FIGS. 2 and 3, one example of system for efficient shipping is shown. This example illustrates five regional shipping company hubs (e.g., transfer points) located in San Francisco 80, Dallas 88, Chicago 82, Atlanta 86, and New York 84. Each hub is represented by a processing device (e.g., a computer configured to interface with memory devices 50A–N and/or 60). FIG. 3 illustrates that a typical shipping charge might be $80.00 for placing a container of goods on a direct flight from San Francisco to New York (or by using a single shipping company), while an indirect routing from San Francisco through Dallas and Atlanta to New York may yield a final cost of only $45.00. (i.e., $20.00 from San Francisco to Dallas, $10.00 from Dallas to Atlanta, and $15.00 from Atlanta to New York). Depending on the schedules involved, the container may take longer to arrive at its final destination, but in many instances customers may be willing to accept longer shipping times in exchange for a lower shipping cost. In this example, each shipping company may have one or more carriers (e.g., similar to carrier 30) that are shipped on a periodic basis to and from each hub city. For example, the shipping company 80 in San Francisco may have one carrier that is shipped daily to Chicago and one container that is shipped daily to Dallas. Regional shipping companies 82 and 88, in Chicago and Dallas respectively, may ship the carriers back also on a periodic basis (e.g., the next day). Similarly, shipping companies 82 and 88 may have carriers that are shipped on a periodic basis to Atlanta and New York. Advantageously, by using standardized containers (e.g., containers 40A–N) and/or standardized carriers (e.g. carrier 30), the transfer of goods at the regional shipping companies may be simplified. Similarly, the use of memory devices 60 and 50A through 50N may further increase the efficiency of the transfer of goods in the shipping hubs.

In one embodiment, each regional shipping company or hub 80–88 may be configured with a container processing apparatus that is directly or indirectly connected to a network 92. In one embodiment, as shown in the figure, network 92 is used to couple the processing apparatuses to a central server 90. While different types of networks may be used, in one embodiment the processing devices at the regional shipping company hubs and central server 90 may be connected via the Internet. In some implementations, the central server 90 may be configured to routinely poll each regional hub to determine availability, shipping times, and prices. Central server 90 may be configured to maintain a database of this information that is periodically updated. A customer wishing to ship an item may then contact one of the regional shipping companies or the central server directly (e.g., via the Internet). The customer may be prompted to provide information about the package to be shipped (e.g., size, weight, origination, final destination, shipping deadline, and any insurance or special handling requirements). If this information is provided to a regional shipping company or hub, the company or hub may then forward the information to central server 90 to query the database for a quote. In response, central server 90 may execute an optimization program configured to search out the most efficient (e.g., lowest cost) routing for the package within the specified time constraints. Central server 90 may also have information about traditional shipping alternatives (e.g., direct routing using one shipping company) for comparison.

FIG. 4: Data File

Turning now to FIG. 4, one embodiment of a data file stored in memory device 50A is shown. In this embodiment, the data file includes the following: a unique item identification number (e.g., a package tracking number) 51, a description of the goods being shipped 60, the weight of the goods being shipped 61, any special shipping instructions (e.g., temperature, humidity, and vibration restrictions) 52, insurance terms (e.g., the insurance carrier, the policy number, the amount of insurance, and any deductible amounts) 55, the original shipping date 62, the arrival deadline 63, the origination location 53, the destination 54, any payment terms 64, information about the sender (e.g., sender's name 65, sender's email address 66, sender's telephone number 69, sender's street address 68, sender's shipping company account number 69), information about the recipient (e.g., recipient's name 65, recipient's email address 66, recipient's telephone number 69, recipient's street address 68, recipient's shipping company account number 69), and information about one or more intermediate destinations (75 through 77). Depending upon the implementation, additional information may also be stored in memory device 50A (for example, fax numbers for the sender and/or recipient). Similarly, less information than is shown in the figure may also be stored in memory device 50A in some embodiments. Advantageously, in some embodiments memory device 50A may be used to simplify payment (e.g., for shipping, for any tariffs or customs charges, or for the goods themselves in a COD arrangement). For example, memory device 50A may include account numbers for the sender 69, and recipient 74. Other possibilities include credit card, debit card, and bank account information. In some embodiments, the data stored in the memory device may be encrypted. The device used to read the data from the memory device (e.g., processing apparatus 198 from FIG. 9 or package processors 322–324 from FIG. 10, as described below) may have a public key or private key usable to decrypt the data in the memory device.

In one embodiment, authorized users of the system may be given a public key stored on a smart card, magnetic swipe card, or other electronic data storage card (e.g., Sony Corporation's Memory Stick™). The data from the memory device may also copied and then sent in email (e.g., in encrypted form) via the Internet to one or more of the parties associated with the shipping transaction (e.g., the originator, the shipping company, and the recipient).

Figure 5:
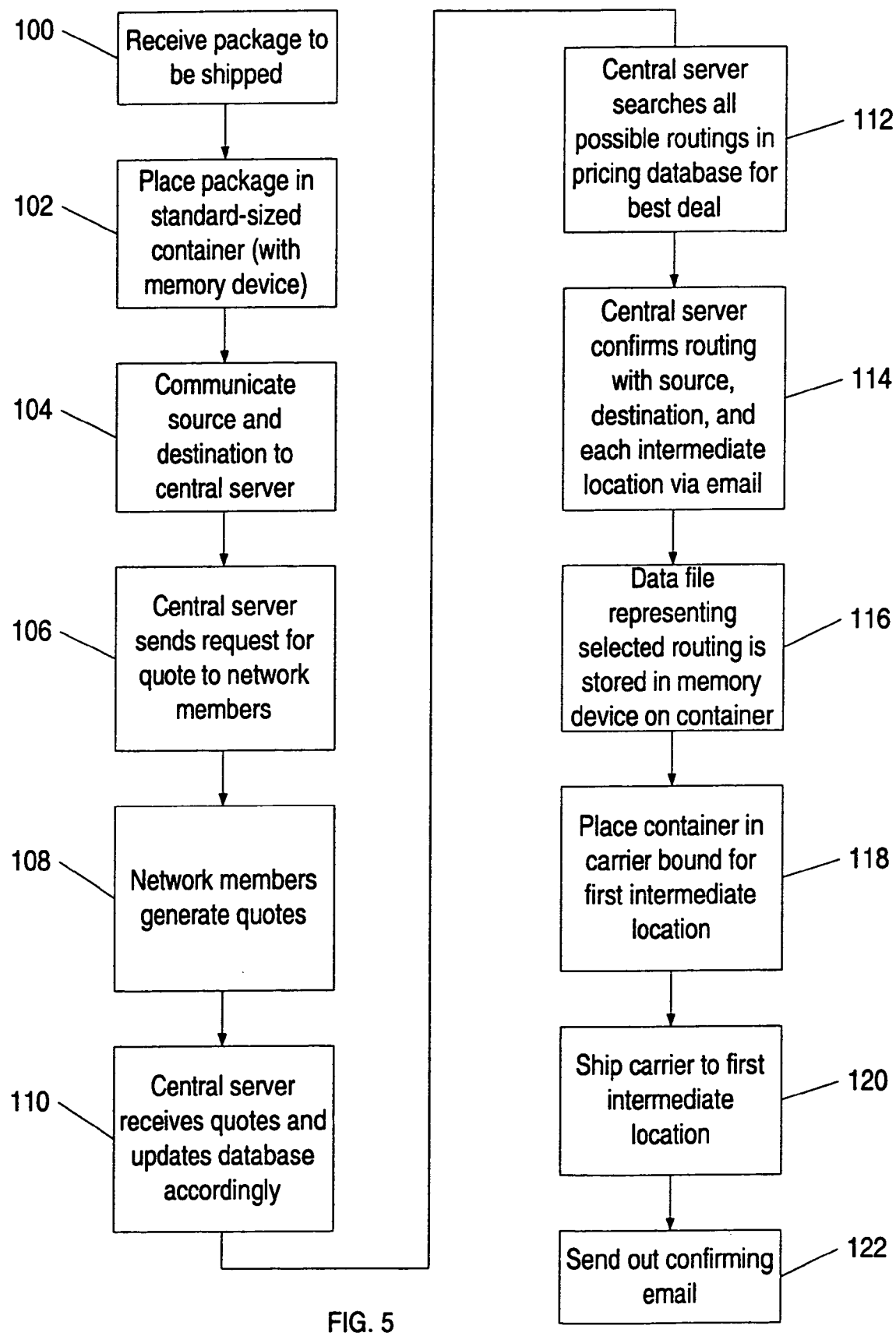
FIG. 5 is a flow chart illustrating one embodiment of a method for efficiently shipping packages.
Figure 6:
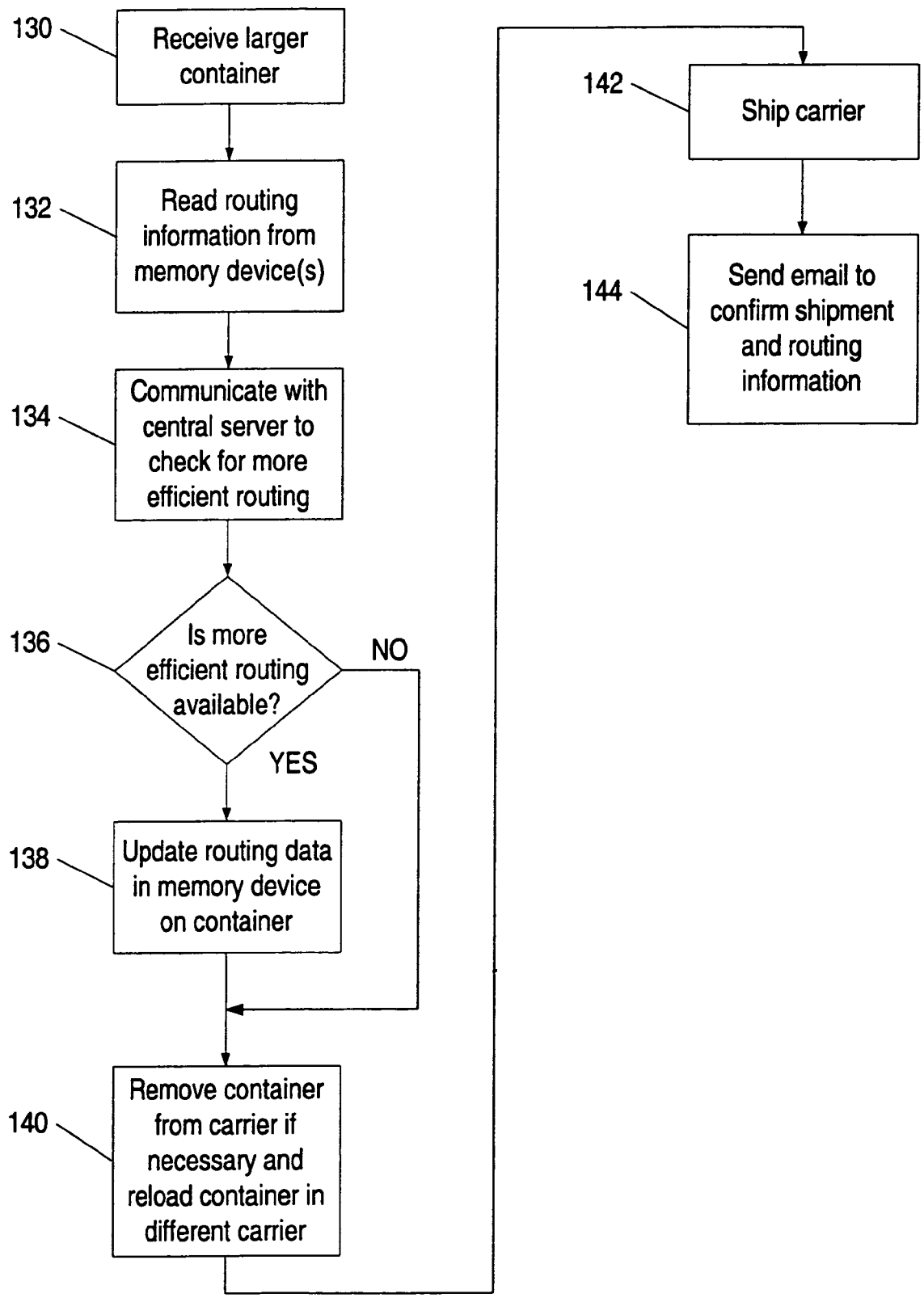
FIG. 6 is a flow chart illustrating another embodiment of a method for efficiently shipping packages.

FIGS. 5–6: Method for Efficient Shipping

Turning now to FIG. 5, one embodiment of a method for efficient shipping is shown. First, a package or allotment of goods to be shipped is received (Step 100). Next, the package or goods are placed inside a standard size shipping container with an attached memory device (such as containers 40A–N with attached memory devices 50A–N) (Step 102). Note, in some cases the container may need not be used (e.g., if the item is already adequately packages in a box that has the same dimensions as containers 40A–N. In these cases, the memory devices may be affixed directly to the item itself.

Next, information about the package to be shipped is transmitted to central server 90 (Step 104). This information may include the origination and destination of the package, information about the type of package being shipped (e.g., the weight, any special shipping requirements such as temperature, humidity, or hazardous materials) and shipping dates (e.g., shipping deadlines). Central server 90 may then be configured to send out a request for quote based on this information to network members (Step 106). In another embodiment, central server 90 may be configured to periodically update the database independent of any request for quotes. Alternatively, in a distributed environment without a central server 90, the originating shipping company may distribute request for quotes directly to network members without central server 90. In response to the request for quote, network members may generate quotes for shipping costs for shipping the package to and from their shipping hub. (Step 108). For example, the shipping company in Dallas (see hub 88 in FIG. 2) may be configured to provide quotes for shipping the package from Dallas to New York and to Atlanta. Similarly, the shipping company in Chicago (see hub 82 in FIG. 3) may be configured to generate quotes for shipping the designated goods from Chicago to Atlanta and New York. As noted above, in some cases more than one container may be needed to ship the package. In these cases, the network members may provide quotes for shipping only a subset of the packages if they do not have enough capacity to handle the entire set of containers or if a price differential is apparent for partial shipment. The central server may be configured to receive all of the quotes and update a database of shipping prices accordingly (Step 110). After the time period for responding to the request for quote has expired, the central server may be configured to search all possible routings in the pricing database to determine the best deal for the customer (Step 112). Depending on the customer's requirements, some routings may be eliminated based on time (e.g., some routings may take too long and thus fail to meet the customer's shipping deadline).

Once the central server has selected a particular routing for the goods to be shipped, it may confirm this routing with the customer, the originating shipping company, the destination, and any intermediate locations/shipping companies (Step 114). This confirmation may be performed via the network (e.g., e-mail or instant messaging). The central server may also be configured to generate a data file that includes information about the goods to be shipped and the selected routing. As noted above, one embodiment of such a data file is shown in FIG. 4. This data file may be transmitted with the confirmation sent out by the central server in Step 114. The originating shipping company may update (if desired) and store a copy of the data file in the memory device that is attached to the container that will be used to ship the goods (Step 116). Next, the originating shipping company may place the container in a carrier 30 that is bound for either the final destination or an intermediate location as specified in the selected routing (Step 118). Selected information about the container may also be stored in the carrier's memory device, if desired. Next, the carrier is shipped to the first intermediate location (Step 120). As part of the shipping process, a confirmation e-mail may be sent out to the central server and one or more of the parties associated with the shipment (e.g., the shipper, any intermediate shipping companies, and the recipient). (Step 122).

Advantageously, central server 90 may be configured to maintain a real time or near real time database of the status of all goods being shipped using the network. For example, a customer or shipping company may enter in a unique identifier that identifies the goods being shipped, and the database may respond by outputting the data file (e.g., as shown in FIG. 4). At each intermediate destination and at the final destination, confirmation of arrival and shipment may be conveyed to the central server which may then update the database accordingly. Similarly, the confirmations may be sent to any parties associated with the shipment (e.g., via e-mail).

Figure 7:
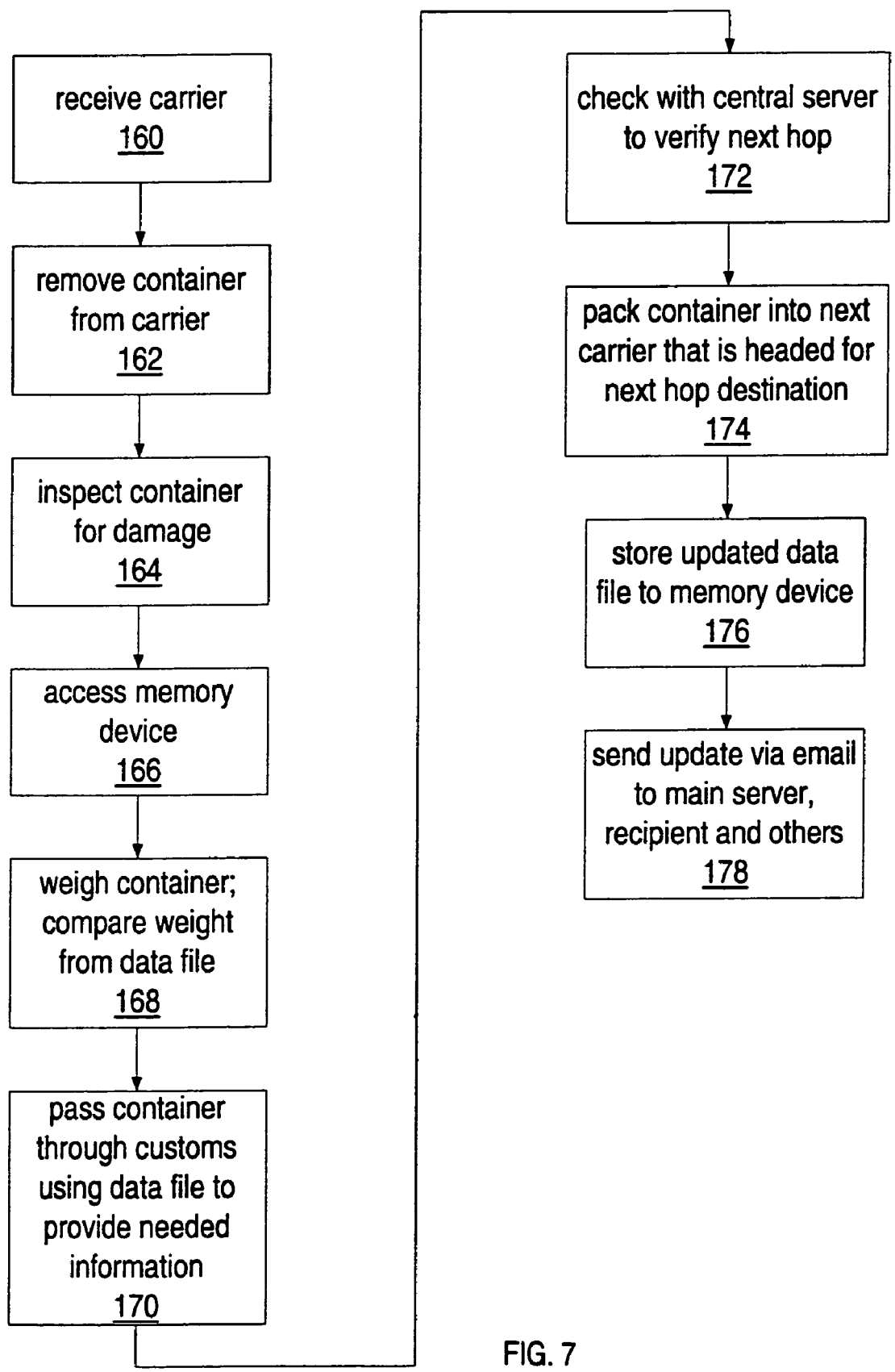
FIG. 7 is a flow chart illustrating yet another embodiment of a method for efficiently shipping packages.

FIGS. 6–7: Handling Packages at Intermediate Destination

Turning now to FIG. 6, a flowchart depicting one portion of one embodiment of a method for efficient shipping is shown. In this figure, details of how the container may be handled upon arriving at an intermediate destination is shown. First, the container is received at the intermediate destination (Step 130). Next, the data file, or at least the routing information, may be read from the memory device attached to the container and/or the carrier (Step 132). Next, the shipping company may be configured to communicate or verify the receipt of the goods using the network. The shipping company may also communicate with the central server to check if more efficient routings from the intermediate destination to the final destination have become available (Step 134). For example, a particular shipment of goods may originally be routed from San Francisco to New York via Dallas and Atlanta. However, by the time that the shipment arrives in Dallas, a more direct routing from Dallas to New York may have become less expensive than a routing through Atlanta. This may be due to changes in airline shipping rates, price wars, the cancellation of other shipments leading to excess capacity, or other factors. Thus, central server 90 may be configured to determine whether or not there is a more efficient routing available. (Step 136). If there is a more efficient routing available, server 90 may be configured to convey this information to the shipping company in Dallas, which may then update the routing information in the memory device 50A affixed to the shipping container (Step 138). Similarly, server 90 may be configured to update the information on the server's database for access by any party to the shipping transaction (e.g., the originator, the final recipient, and any shipping companies involved in the transaction). Once the routing for the remainder of the shipment has been determined, the regional shipping company (e.g., the shipping company that has received the container in Dallas), may remove the container from the carrier and reload the container into a different carrier that is destined for the next intermediate destination or the final destination (Step 140). As part of this process, the shipping company may also update the memory device on the carrier to reflect the newly added container. Next, the carrier is shipped (Step 142), and a confirmation may be transmitted to central server 90 and/or one or more of the parties to the transaction (Step 144). In one embodiment, the confirmation may be sent as an e-mail, instant message via the Internet, or a text-to-speech message via telephone. As noted above, the confirmation may include a copy of the updated data file.

Turning now to FIG. 7, another embodiment of a method for handling the containers at an intermediate or final destination is shown. This embodiment assumes that additional processing is performed on the shipped goods to ensure that the goods have arrived in acceptable condition. First, the carrier is received (Step 160). Next, the container may be removed from the carrier (Step 162). The container may be visually inspected for damage (Step 164). For example, in one embodiment digital cameras may be used to take pictures of the container and/or goods within the container to verify their condition. In some implementations, these digital image files may be appended to the data file and transmitted to central server 90. In another embodiment, automated scanning devices may be used to inspect the container for damage. For example, each container may have a pattern imprinted on its sides. Any damage to the container may (e.g., dents, or gouges) may be detected as by a digital camera that scans for the imprinted pattern. For example, a regularly spaced grid or series of lines may be imprinted on the surface of the carrier (e.g., a black and white bar code). Damage to the device will most likely result in variations to the patter, and the processing unit may be configured to detect these variations and signal a problem to the operator or the central server.

Similarly, if the container's memory device is outfitted with an environmental sensor, then the processing unit may be configured to read the contents of the memory device to ensure that the container has not experienced any environmental extremes. For example, assuming that there are delicate glass components in the container, and if the environmental sensor detects that a vibration exceeding a predetermined maximum threshold has occurred, then the processing unit may signal an alert the operator. The operator may then notify the shipper and recipient and possibly check the shipped items for damage. Advantageously, if the items have been damaged due to the vibration, the container may be returned to directly to the originating party from the intermediate destination without incurring the additional cost and wasted time of shipping the container all the way to the final destination before finding out that the items inside have been damaged.

Once the container has been inspected for damage, any damage or problems may be noted and appended into the data file. As noted above, the data file may be stored to the memory device and also conveyed to central server 90. In addition to damage, the container's weight may be compared with the memory device's weight information stored in the data file. (Step 168). While the use of weight may be optional, it may be particularly advantageous in international shipping where concerns such as smuggling often arise. By insuring that the weight of the package as received is the same as the weight of the package as shipped, customs officials may be less concerned with additional items being smuggled in the container and thus less likely to open the container and thereby delaying shipment. (Step 168). Additional information to assist in the customs process may also be read from the data file (Step 170). For example, a declaration of the type of goods in the container may be read from the memory device.

As previously noted, the central server may be contacted to verify the next intermediate destination (e.g., to check for cheaper routings). (Step 172). Next, the container is packed into a different carrier (if necessary) that is headed to the next intermediate destination or the final destination (Step 174). As noted above, in the event that multiple containers have been shipped together, the containers may take different routings to the final destination. The updated data file may be stored to the memory device on the container and/or carrier (Step 176). Similarly, the updated data file and/or a confirmation of shipment may be conveyed to central server 90 and any party to the shipping transaction (Step 178).

Figure 8:
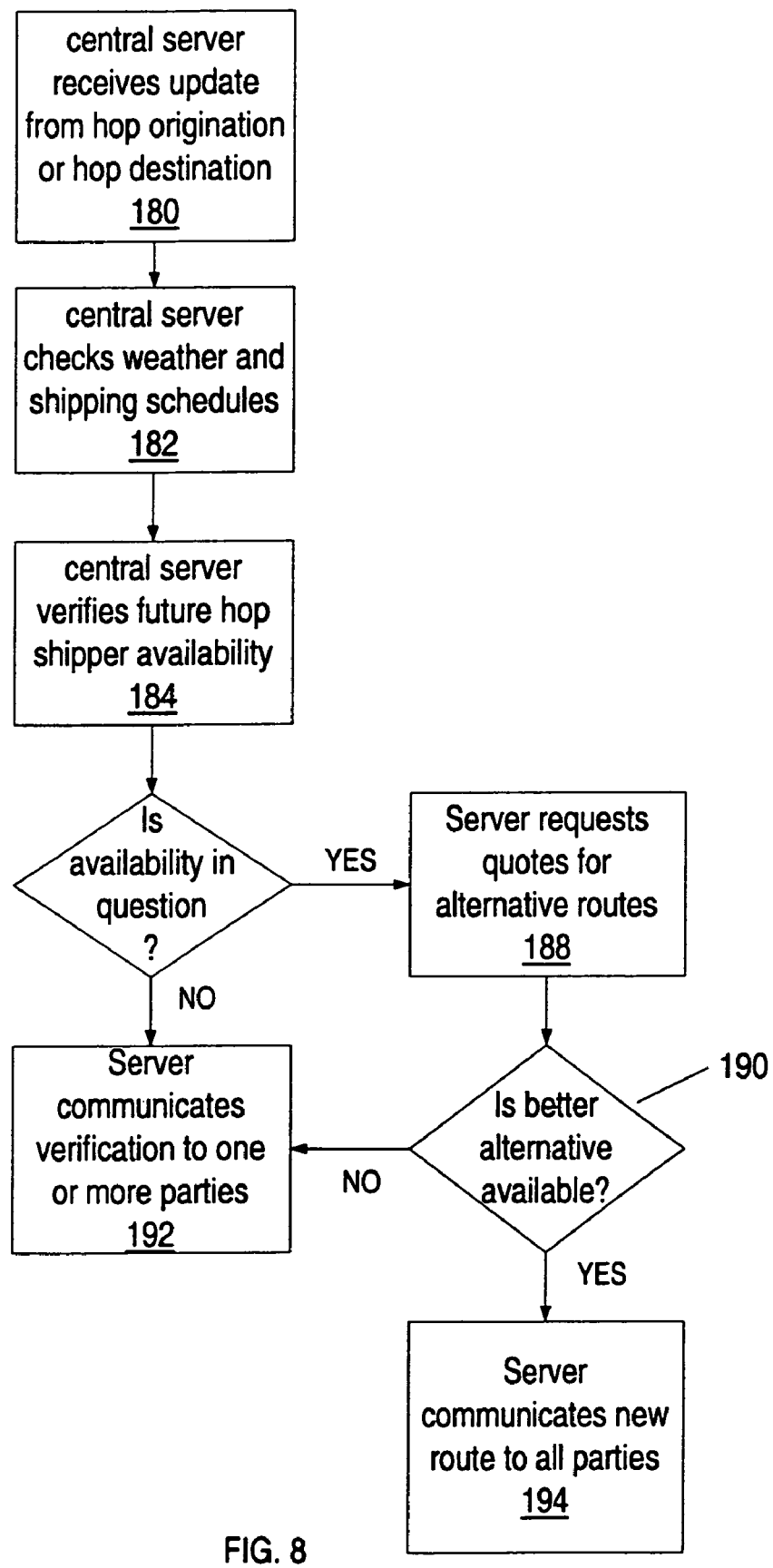
FIG. 8 is a flow chart illustrating another embodiment of a method for efficiently shipping packages.

FIG. 8: Operating Central Server

Turning now to FIG. 8, one embodiment of a method for operating central server 90 is illustrated. In this embodiment, central server 90 may be configured to receive updates from intermediate destinations (Step 180). Central server 90 may be configured to periodically check shipping schedules for subsequent intermediate destinations (Step 182) to verify the availability and/or feasibility of the future intermediate destination (Step 184). If availability of shipment through one or more of the subsequent intermediate destinations is in question (Step 186), then the server may be configured to request quotes for alternate routes (Step 188). If one or more better alternative routes are available (Step 190), then the server may then communicate the newly selected route to all parties to the shipping transaction (Step 192). For example, in one embodiment the central server may be configured to check weather forecasts and/or travel advisories for selected intermediate destinations. If Chicago is an intermediate destination for a particular shipment scheduled to arrive on the 22nd of January, and if Chicago is experiencing a serious blizzard with travel advisories on the 21st of January just prior to initiation of the shipment, the central server may be configured to attempt to re-route the shipment to avoid the weather problems in Chicago. Similarly, if the regional shipping company in Chicago has indicated that it has a two-day backlog of packages to ship out, the central server may use that information to find an alternate route. If, however, no issues concerning availability of shipment at intermediate destinations arise, or if no better alternatives are available, then the central server may simply be configured to communicate a verification of the original route to one or more of the parties to the shipping transaction (Step 192).

Figure 9:
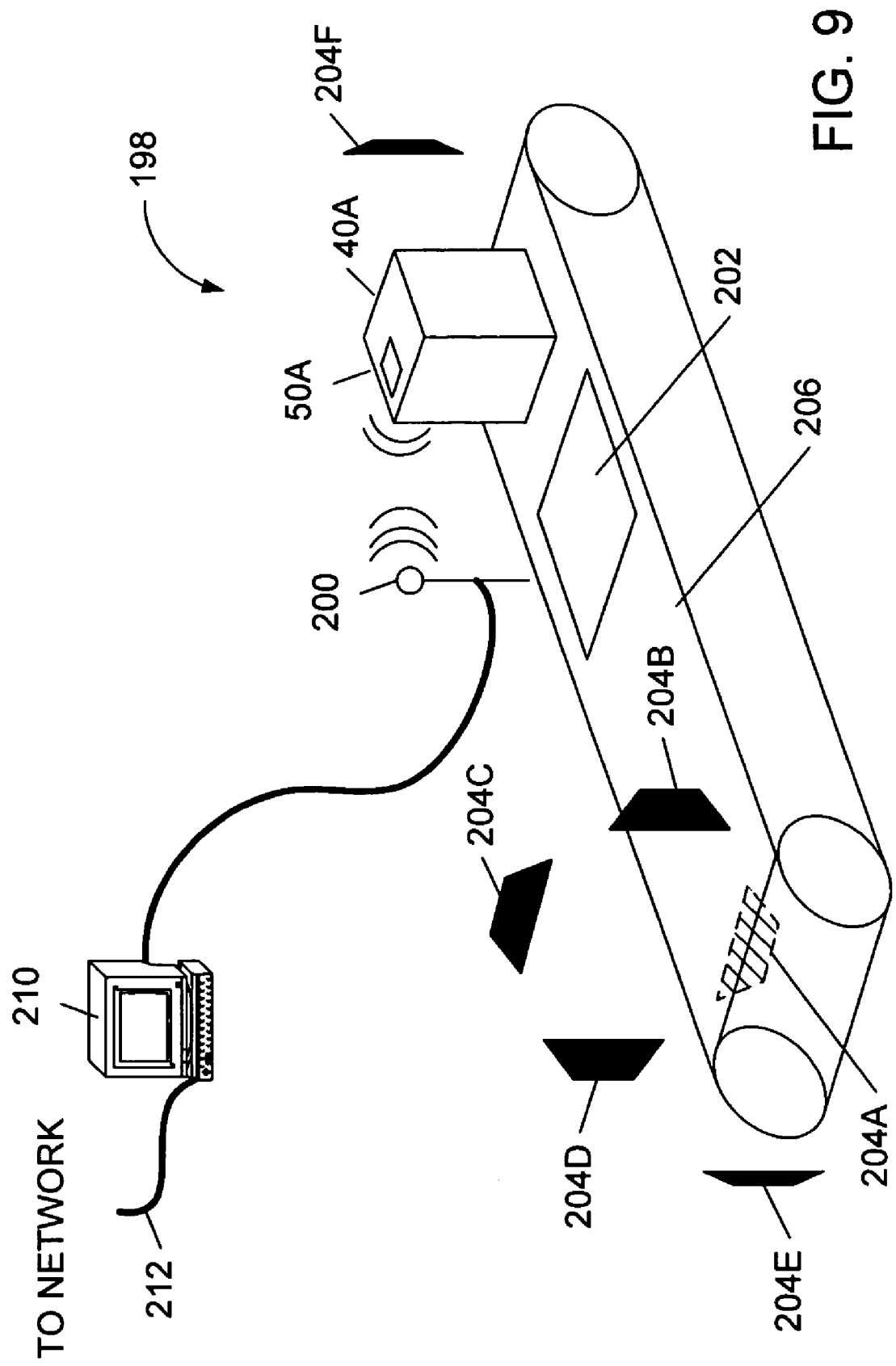
FIG. 9 illustrates one embodiment of an apparatus for processing packages.

FIG. 9: Apparatus for Package Processing

Turning now to FIG. 9, one embodiment of an package processing apparatus 198 for efficiently handling shipment of containers (e.g., container 40A) is shown. In this embodiment, the apparatus (also referred to herein as a package processing unit) comprises a conveyor belt 206. As shown in the figure, conveyor belt 206 is configured to convey container 40A over a weighing device 202. The apparatus may further comprise a communications device 200 configured to communicate with, and read the contents of, memory device 50A.

In some embodiments, the apparatus may further comprise one or more digital cameras (e.g., 204A through 204F). As previously noted, these digital cameras may be configured to capture images of the carrier, container, and/or the item itself. In some embodiments (assuming there is enough storage available in the memory device), these images may be stored in the memory device by the package processing unit using communications device 200 or they may be communicated to the central server via the network. Note, this figure merely illustrates one possible embodiment for the apparatus and other embodiments are possible and contemplated. For example, in one embodiment the apparatus may be implemented as a handheld device without conveyor belt 206. The handheld device may include communications device 200 to communicate with memory device 50A, and a digital camera configured to capture images of the container 40A. Other embodiments may be configured without digital cameras. Communications device 200 may, for example, be a wireless link, a physical cable that connects to memory device 50A, or a removable media reader (e.g., a CD-RW drive).

Advantageously, the package processing apparatus described above may be installed at locations such as ports, warehouses, airports, distribution centers, and shipping companies. The operation of the apparatus may advantageously be automated (e.g., with a mechanical arm to automatically remove and insert containers into carriers and/or to automatically read and write data to the memory device). The apparatus may further comprise an interface to a computer system 210. Computer system 210 may in turn be connected to a network (e.g., the Internet) by link 212. The computer system may communicate with the apparatus in order to convey the captured data (e.g., from memory device 50A and digital cameras 204A–F) to central server 90. As noted above, in other embodiments the apparatus may include an internal computer or microprocessor with a built-in wireless network connection and scanning device.

Advantageously, by accessing the data files stored in central server 90's database (e.g., by using an Internet website), any party to the shipping transaction may be able to immediately determine where the package is and which shipping company is currently in charge of the package. As previously noted, additional information may also be available (e.g., any damage that the device may have sustained or any environmental extreme the container may have experienced).

Another potential advantage of some embodiments of the system and method described above is the ability of any party to the transaction to alter the final destination conveniently. For example, a package being shipped from Tokyo to New York may have the final street address altered by accessing the central server and entering the new final destination address. In a traditional system wherein the destination address is affixed to the package in an unchangeable manner, there is no convenient way to update the final delivery address. In contrast, using the method described above the updated address in central server's database may be downloaded to the memory device on the carrier or container at any intermediate destination. Confirmation of the final destination address change may be automatically sent to all relevant parties in the shipping transaction.

In some embodiments, the central server may be configured to automatically notify one or more parties to the shipping transaction upon the occurrence of predetermined events. For example, once the package reaches a particular intermediate destination or the final destination, the central server upon receiving confirmation of this may be configured to automatically contact the designated recipient (e.g., by an automated call to a telephone or cell phone number, or by e-mail, paging, or instant messaging). Similarly, local trucking companies or shipping companies may be notified automatically as soon as the package arrives at a particular intermediate or final destination.

In some embodiments, the unique identification number associated with a particular item may be assigned by central server 90. In other embodiments, the local shipping company may assign this number after verifying that there is no other package currently using the number in central server 90's database. In some embodiments, the unique ID number may be shared with one or more shipping companies that handle the package from its origination to its final destination. For example, assuming a package is shipped by airlines A and then delivered by trucking company B, airline A and trucking company B may both be provided access central server 90 to read the data file. The unique identification number may be selected in a format such that it is useable both by airline A's and trucking company B's computers systems. In one embodiment, central server 90 may be configured to contact the servers of airline A and trucking company B in order to select a unique identifier that is also useable by those company's computer systems. Advantageously, this unique identifier may also be used to control billing receipts and customs records for the shipped item.

In one embodiment, central server 90 may be implemented as a number of different servers (e.g., one server in each country serviced by shipping companies that are part of the network). Advantageously, if the number of e-mails or instant messages generated by the network of shipping companies becomes to large, distributing the processing among multiple servers may advantageously reduce the e-mail traffic burden. The data file associated with a particular package may be stored only on the server residing in the originating country. In one embodiment, the data file may be formatted using XML, SGML, HTML, or another type of mark-up language or data file format. Advantageously, XML offers several potential advantages including the ability to format data such that it may be more easily imported into SQL databases.

Figure 10:
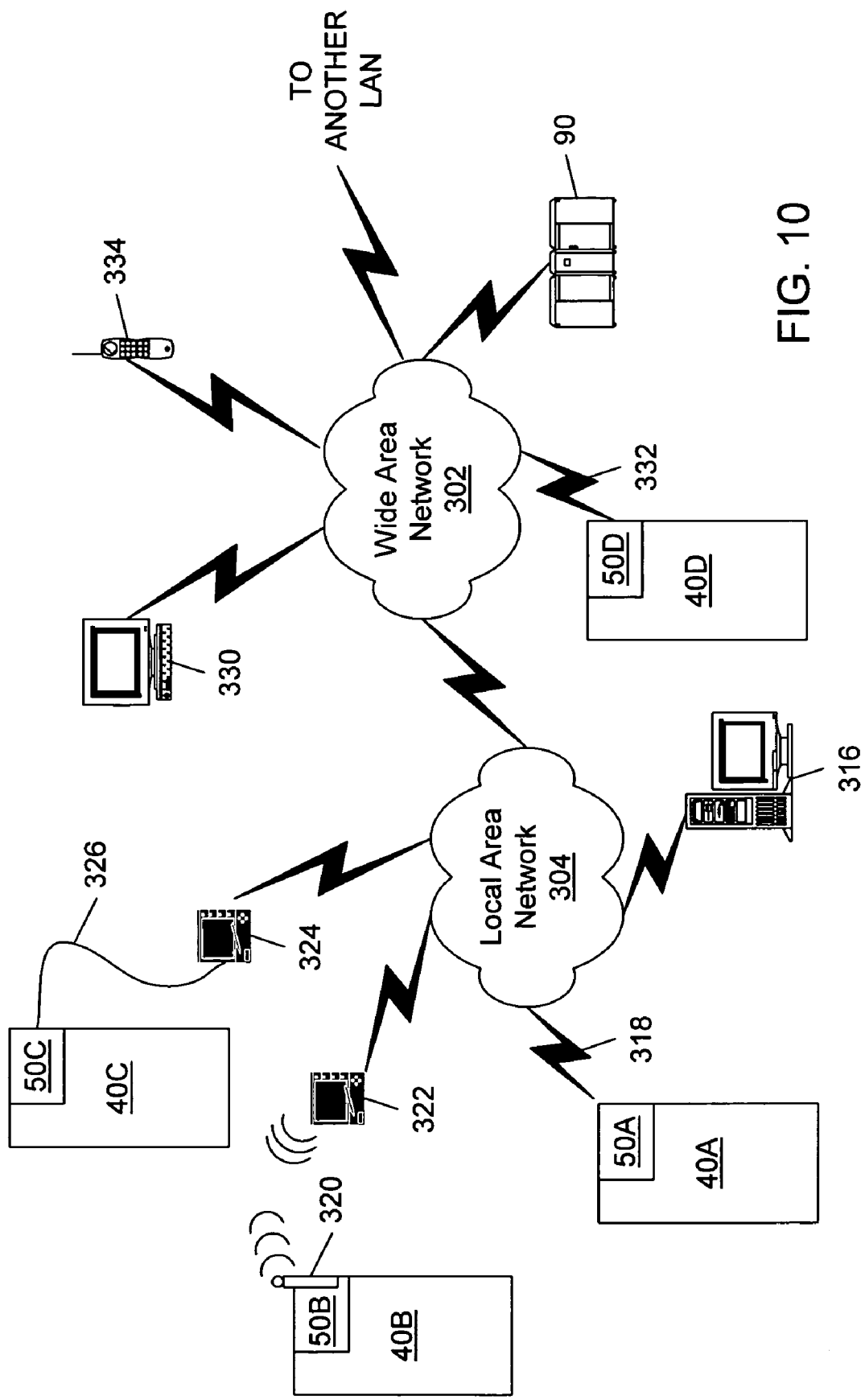
FIG. 10 illustrates one embodiment of a network usable to implement the systems and methods described herein.

FIG. 10: Wide Area Network

Turning now to FIG. 10, one embodiment of a wide area network (WAN) that may be used to implement the system described above is shown. WAN 302 is a network that spans a relatively large geographical area. The Internet is an example of WAN 302. WAN 302 typically includes a plurality of computer systems which are interconnected through one or more networks. Although one particular configuration is shown in the figure, WAN 302 may include a variety of heterogeneous computer systems and networks which are interconnected in a variety of ways and which run a variety of software applications.

One or more local area networks (LANs) 304 may be coupled to WAN 302. A LAN 304 is a network that spans a relatively small area. Typically, a LAN 304 is confined to a single building or group of buildings (e.g., one airport or shipping hub). Each node (i.e., individual computer system or device) on a LAN 304 preferably has its own CPU with which it executes programs. LAN 304 allows many users to share devices (e.g., printers) as well as data stored on file servers. The LAN 304 may be characterized by any of a variety of types of topology (i.e., the geometric arrangement of devices on the network), of protocols (i.e., the rules and encoding specifications for sending data, and whether the network uses a peer-to-peer or client/server architecture), and of media (e.g., twisted-pair wire, coaxial cables, fiber optic cables, radio waves).

Each LAN 304 includes a plurality of interconnected computer systems and optionally one or more other devices: for example, one or more personal computers 316, and one or more package processing apparatuses 322–324. Package processors 322–324 may, for example, be hand-held devices (e.g., used in connection with a forklift, crane, or automated loading and unloading station as shown in FIG. 1K) or conveyor-belt devices as previously described. As illustrated in the figure, some package processors (e.g., processor 322) may be configured to communicate with container memory devices (e.g., container 40B) via a wireless link 320. Other package processors (e.g., processor 324) may communicate with the memory device 50C of a received container 40C by a physical link 326. As also noted above, in some embodiments, some configurations of container 40A may have a memory device 50A that is configured to communicate directly with LAN 304 and/or WAN 302 (see e.g., container 40D and memory device 50D). For example, LAN 304 may constructed at a shipping hub (e.g., an airport, dock or warehouse) and may be configured to use a wireless access protocol that supports the dynamic addition and remove of devices (e.g., using Sun Microsystems Inc.'s Jini® protocol). Whenever a container is brought within range of the wireless LAN, then the containers' memory devices (e.g., using internal processors and wireless links such as link 320) may access the network and communicate their data.

Central server 90 may coupled to multiple LANs via WAN 302. As described above, central server 90 may be configured to convey email verification messages to one or more computers (e.g., personal computers 316 and 330) connected to WAN 302 or LAN 304. Central server 90 may also be configured to send text of voice messages (e.g., pages) to cell phones (e.g., cell phone 334) or pages as specified by the parties to shipping transaction.

Figure 11:
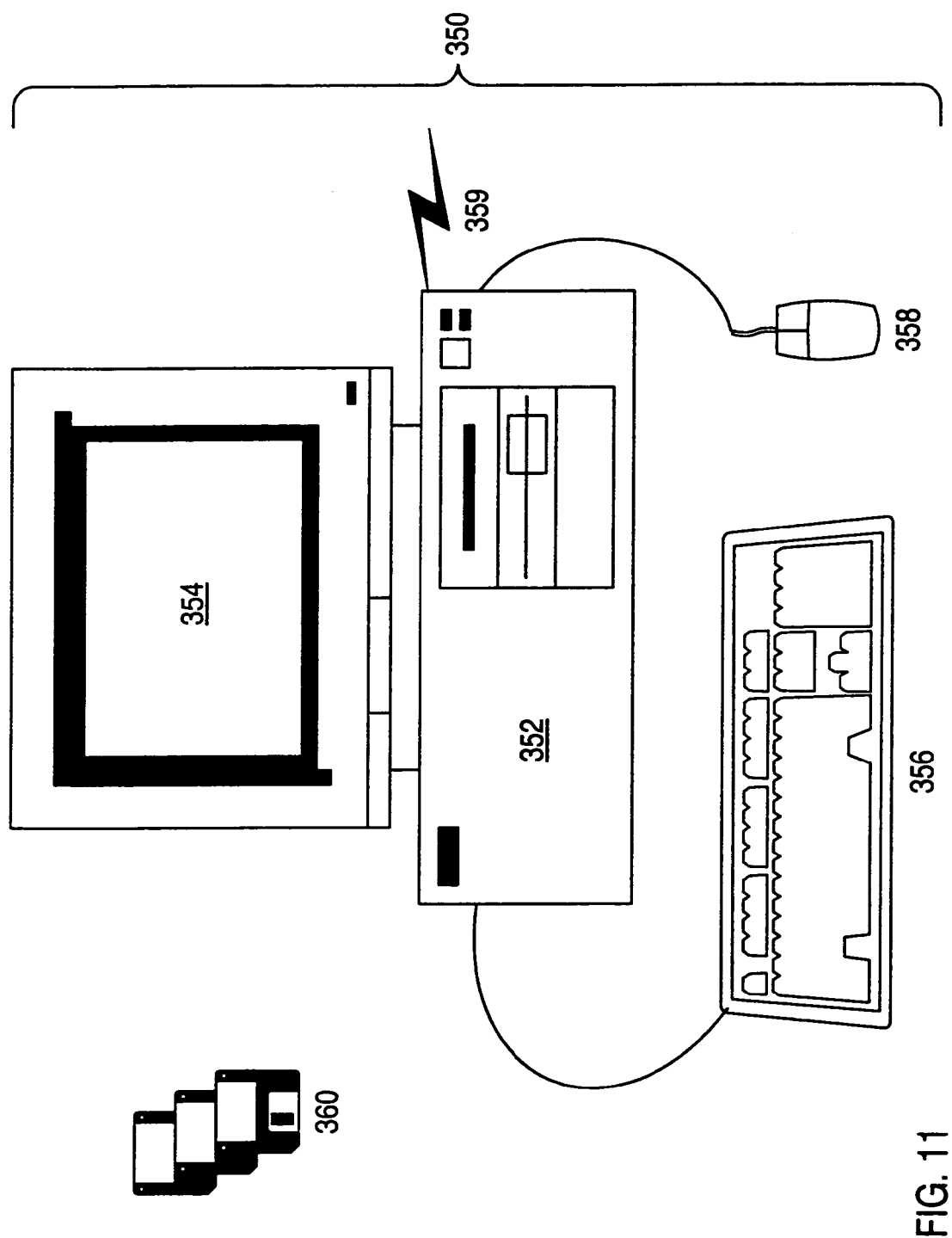
FIG. 11 illustrates one embodiment of a computer system usable to implement the systems and methods described herein.

FIG. 11: Typical Computer System

FIG. 11 illustrates a typical computer system 350, which is suitable for implementing various embodiments of the systems and methods described above. Each computer system 350 typically includes components such as a CPU 352 with an associated memory medium such as floppy disks 360, CD-ROMs, or DVDs (not shown). The memory medium may store program instructions for computer programs, wherein the program instructions are executable by the CPU 352. The computer system 350 may further include a display device such as a monitor 354, an alphanumeric input device such as a keyboard 356, communication device such as a modem 359 and a directional input device such as a mouse 358.

In one embodiment, the computer system 350 may be configured to execute a computer program to access containers' memory devices using one or more interfaces as described herein. In another embodiment, the computer system 350 may be a central server (e.g., such as central server 90) operable to execute a computer programs to create and manage the database of routing information as described herein. Other embodiments of the computer system 350 are also possible and contemplated.

The computer system 350 preferably includes a memory medium on which computer programs according to various embodiments may be stored. The term "memory medium" is intended to include an installation medium, e.g., a CD-ROM, or floppy disks 360, a computer system memory such as DRAM, SRAM, EDO RAM, Rambus RAM, or a non-volatile memory such as a magnetic media, e.g., a hard drive, or optical storage. The memory medium may include other types of memory as well, or combinations thereof. In addition, the memory medium may be located in a first computer in which the programs are executed, or may be located in a second different computer, which connects to the first computer over a network. In the latter instance, the second computer provides the program instructions to the first computer for execution. The computer system 350 may also include a time keeping device such as a real-time clock. The real-time clock of the computer system 350 may be, periodically or on demand, synchronized with a global standard time clock. Also, the computer system 350 may take various forms, including but not limited to a personal computer system, mainframe computer system, workstation, network appliance, Internet appliance, personal digital assistant (PDA), Internet enabled cellular telephones, or any other similar device. In general, the term "computer system" can be broadly defined to encompass any device having a processor, which executes instructions from a memory medium.

The computer system's memory medium preferably stores a software program or programs for performing the methods for efficient shipping as described herein. The software program(s) may be implemented in any of various ways, including procedure-based techniques, component-based techniques, and/or object-oriented techniques, among others. For example, the software program may be implemented using ActiveX controls, programming languages such as C++, Java, Visual Basic, object oriented software based on COM/DCOM and/or CORBA objects, JavaBeans, Microsoft Foundation Classes (MFC), browser-based applications (e.g., Java applets), traditional programs, or other technologies or methodologies, as desired.

Although the embodiments above have been described in considerable detail, other versions are possible. Numerous variations and modifications will become apparent to those skilled in the art once the above disclosure is fully appreciated. It is intended that the following claims be interpreted to embrace all such variations and modifications.

What is claimed is:

1. A method for shipping goods, wherein the method comprises:
   a central server receiving via a network a request to ship an item from an origination to a final destination;
   the central server searching a database for a most inexpensive routing, wherein the most inexpensive routing includes using two or more different shipping companies and one or more intermediate destinations;
   the central server generating a data file comprising at least the following:
      intermediate destination information identifying the one or more intermediate destinations, and
      final destination information identifying the final destination;
   the central server transferring the data file over a network; and
   storing the data file in a memory device that accompanies the item.

2. The method as recited in claim 1, wherein the memory device is configured to allow the data file to be updated at one or more of the intermediate destinations.

3. The method as recited in claim 1, further comprising packing the item in a container for shipping, wherein the container is configured to fit with multiple other containers in a carrier.

4. The method as recited in claim 1, further comprising forwarding copies of at least a portion of the data file via the network to one or more parties involved in the shipping, wherein the parties include at least an originator of the request to ship the item, a recipient of the item at the final destination, and two or more shipping companies.

5. The method as recited in claim 1, further comprising forwarding copies of the data file via the network to one or more predetermined email addresses.

6. The method as recited in claim 1, further comprising shipping the item using the least expensive routing.

7. The method as recited in claim 1, further comprising:
   packing the item in a container;
   inserting the container in a first carrier with a first set of additional containers bound for a first of the one or more intermediate destinations; and
   shipping the first carrier to the first intermediate destination.

8. The method as recited in claim 1, further comprising:
   receiving the carrier at the first intermediate destination;
   removing the container from the carrier;
   inserting the container into a different carrier with a second set of additional containers bound for a second intermediate destination or the final destination; and
   shipping the second carrier to the second intermediate destination or the final destination.

9. The method as recited in claim 1, wherein the data file further comprises contact information for one or more shipping companies that will handle the item.

10. The method as recited in claim 1, further comprising storing the data file on a server connected to the network, wherein the server provides access to the data file via the network.

11. The method as recited in claim 1, wherein the data file further comprises item weight information.

12. The method as recited in claim 1, wherein the data file further comprises item handling information.

13. The method as recited in claim 1, wherein the data file further comprises item content information.

14. The method as recited in claim 1, wherein the data file further comprises payment information.

15. The method as recited in claim 1, wherein the data file further includes one or more digital images of the item before, during, or after shipping.

16. The method as recited in claim 1, wherein the data file further includes one or more digital images of the item showing the physical condition of the item upon receipt at one or more intermediate destinations.

17. The method as recited in claim 1, wherein the memory device further comprises a temperature sensor, wherein the temperature sensor is configured to periodically measure and store temperature readings in the data file.

18. The method as recited in claim 1, wherein the memory device further comprises a humidity sensor, wherein the physical humidity sensor is configured to periodically measure and store humidity readings in the data file.

19. The method as recited in claim 1, wherein the memory device further comprises an environmental sensor, wherein the environmental sensor is configured to periodically measure and store in the data file information about one or more environmental factors that the item experiences during shipment.

20. The method as recited in claim 1, wherein the memory device further comprises a vibration sensor, wherein the vibration sensor is configured to record any vibrations greater than a preprogrammed threshold in the data file.

21. The method as recited in claim 1, wherein the memory device is coupled to a wire-less communications device.

22. The method as recited in claim 1, further comprising:
   detecting one or more obstacles to on-time delivery of the item, searching the database for a new least expensive routing that avoids the obstacles; and updating the data file to reflect the new least expensive routing.

23. The method as recited in claim 1, further comprising updating the data file on the central server to reflect arrival of the item at one or more of the intermediate destinations.

24. The method as recited in claim 1, wherein the memory device is a flash memory device.

25. The method as recited in claim 1, wherein the memory device is a CD-RW.

26. The method as recited in claim 1, wherein the database include price information and delivery time information.

27. The method as recited in claim 1, further comprising:
    detecting one or more obstacles to on-time delivery of the item,
    soliciting new quotations for shipping the item from one of the intermediate locations to the final destination by transmitting a supplemental request for quotation via the network;
    receiving additional responses to the supplemental request for quotation via the network;
    selecting an alternate shipping route for the item based on the additional responses; and
    confirming the selected alternate shipping route via the network.

28. The method as recited in claim 27, wherein the obstacles include travel advisories for one or more of the intermediate locations.

29. The method as recited in claim 27, wherein the obstacles include shipping backlogs.

30. The method as recited in claim 1, further comprising updating the data file on the central server to reflect the item's arrival at the final destination.

31. The method of claim 1, wherein the item is included in a group of items to be shipped from the origination to the final destination, the method further comprising the central server selecting one shipping route on which to ship a subset of the group of items and another shipping route on which to ship a remainder of the group of items.

32. A computer program embodied on a computer-readable medium, wherein the computer program is configured to:
    receive a shipping request via a network for an item to be shipped from an origination to a final destination;
    search a database of shipping information;
    select a shipping route for the item based on the shipping information included in the database, wherein the shipping route comprises one or more intermediate destinations and uses two or more different shipping companies;
    confirm the selected shipping route via the network;
    generate a data file comprising at least the following:
        a unique item identifier,
        origination information,
        intermediate destination information, and
        final destination information;
    transfer the data file via the network; and
    store the data file in a memory device that accompanies the item, wherein the memory device is configured to allow the data file to be updated at one or more of the intermediate destinations.

33. The computer program of claim 32, wherein the computer program is further configured to maintain and update the database by sending requests for quotes using the network.

34. A system comprising:
    a database of shipping information;
    a central server coupled to the database and configured to select a shipping route for an item in response to querying the database, wherein the central server is configured to generate a data file including information identifying an origination, destination, and intermediate destination comprised in the shipping route; and
    a memory device configured to be coupled to the item and configured to receive and store a copy of the data file generated by the central server.

35. The system of claim 34, wherein the central server is configured to update the database in response to receiving one or more responses to a request for quote from one or more shipping companies.

36. The system of claim 34, wherein the central server is configured to confirm the shipping route prior to providing the data file to the memory device.

37. The system of claim 34, wherein the central server is configured to receive confirmation of arrival of the item at the intermediate destination and to responsively update the data file to indicate that the item has arrived at the intermediate destination.

38. The system of claim 37, wherein the central server is configured to send an email indicating arrival of the item at the intermediate destination to a party involved in shipping the item in response to receiving the confirmation.

39. The system of claim 37, wherein the central server is configured to search the database for a less expensive shipping route from the intermediate destination to the final destination in response to the item arriving at the intermediate destination.

40. The system of claim 34, further comprising a processing apparatus located at the intermediate destination, wherein the processing apparatus is configured to update the data file stored on the memory device in response to the item arriving the intermediate destination.

41. The system of claim 34, wherein the central server is configured to select a least expensive shipping route.

42. The system of claim 34, wherein the data file further comprises contact information for one or more shipping companies that will handle the item along the shipping route.

43. The system of claim 34, wherein the central server is configured to provide access to the data file via the network.

44. The system of claim 34, wherein the data file further comprises item weight information.

45. The system of claim 34, wherein the data file further includes one or more digital images of the item before, during, or after shipping.

46. The system of claim 34, wherein the data file further includes one or more digital images of the item showing the physical condition of the item upon receipt at the intermediate destination.

47. The system of claim 34, wherein the memory device further comprises an environmental sensor, wherein the environmental sensor is configured to periodically measure and store in the data file information about one or more environmental factors that the item experiences during shipment.

48. The system of claim 34, wherein the central server is configured to detect one or more obstacles to on-time delivery of the item, to responsively search the database for a new least expensive routing that avoids the one or more obstacles; and to update the data file to indicate the new least expensive routing.

49. The system of claim 48, wherein the central server is configured to request new quotations for shipping the item from an intermediate destination to the final destination in response to detecting the one or more obstacles and to responsively receive one or more responses to the request via the network; wherein the central server is configured to update the database to reflect the responses to the request.

50. The system of claim 34, wherein the central server is configured to update the data file to reflect arrival of the item at the final destination.

51. The system of claim 34, wherein the item is included in a group of items, and wherein the central server is configured to select different shipping routes on which to ship different subsets of the group of items.

52. The method of claim 27, further comprising the central server updating the database in response to said receiving the additional responses.

* * * * *